(12) United States Patent
Momcilovic et al.

(10) Patent No.: US 11,055,519 B1
(45) Date of Patent: Jul. 6, 2021

(54) ACTIVE MARKER STROBING FOR PERFORMANCE CAPTURE COMMUNICATION

(71) Applicant: Weta Digital Limited, Wllington (NZ)

(72) Inventors: Dejan Momcilovic, Wellington (NZ); Jake Botting, Wellington (NZ)

(73) Assignee: WETA DIGITAL LIMITED, Wellington (NZ)

( * ) Notice: Subject to any disclaimer, the term of this patent is extended or adjusted under 35 U.S.C. 154(b) by 0 days.

(21) Appl. No.: 17/163,275

(22) Filed: Jan. 29, 2021

Related U.S. Application Data

(60) Provisional application No. 62/983,523, filed on Feb. 28, 2020, provisional application No. 63/072,081, filed on Aug. 28, 2020, provisional application No. 63/072,082, filed on Aug. 28, 2020.

(51) Int. Cl.
*G06K 9/00* (2006.01)
*G06K 9/46* (2006.01)
*G06T 7/20* (2017.01)
*H04N 5/235* (2006.01)
*H04N 5/232* (2006.01)
*G06T 7/70* (2017.01)

(52) U.S. Cl.
CPC ....... *G06K 9/00342* (2013.01); *G06K 9/4661* (2013.01); *G06T 7/20* (2013.01); *G06T 7/70* (2017.01); *H04N 5/2353* (2013.01); *H04N 5/23232* (2013.01); *G06T 2207/30196* (2013.01); *G06T 2207/30204* (2013.01)

(58) Field of Classification Search
CPC ............................ G06K 9/2036; H01S 5/4087
See application file for complete search history.

(56) References Cited

U.S. PATENT DOCUMENTS

| 6,324,296 B1 | 11/2001 | McSheery |
| 10,373,517 B2* | 8/2019 | Becker ................. G09B 19/003 |
| 10,573,050 B1 | 2/2020 | Liu |
| 10,593,101 B1 | 3/2020 | Han |

(Continued)

OTHER PUBLICATIONS

Nageli et al., "Flycn: real-time environment-independent multi-view human pose estimation with aerial vehicles", 2018 (Year: 2018).

(Continued)

*Primary Examiner* — Hadi Akhavannik
(74) *Attorney, Agent, or Firm* — Trellis IP Law Group, PC

(57) ABSTRACT

The present description relates to light patterns used in a live action scene of a visual production to encode information associated with objects in the scene, such as movement and position of the objects. A data capture system includes active markers that emit light of a particular wavelength in pre-defined strobing patterns. In some implementations, the active markers are instructed to emit an assigned signature pattern of light through a signal controller sending signals to a control unit. Various components are synchronized such that pulsing of light corresponds to time slices and particular frames captured by the performance capture system. The data representing the pattern is embedded in illuminated and blank frames. Frames showing the light pattern are analyzed to extract information about the active markers, such as identification of the active markers and objects to which they are attached.

20 Claims, 13 Drawing Sheets

(56) References Cited

U.S. PATENT DOCUMENTS

| | | | |
|---|---|---|---|
| 10,657,704 B1 | 5/2020 | Han | |
| 10,701,253 B2 | 6/2020 | Knoll | |
| 10,812,693 B2 | 10/2020 | Estebecorena | |
| 2008/0246694 A1* | 10/2008 | Fischer | G02B 30/34 345/9 |
| 2009/0270193 A1* | 10/2009 | Stremmel | A63D 5/04 473/55 |
| 2011/0025853 A1 | 2/2011 | Richardson | |
| 2015/0356737 A1* | 12/2015 | Ellsworth | H04N 5/247 348/169 |
| 2017/0305331 A1* | 10/2017 | Soehner | B60Q 1/1423 |
| 2017/0366805 A1* | 12/2017 | Sevostianov | H04N 13/366 |
| 2018/0131880 A1* | 5/2018 | Hicks | H04N 5/33 |
| 2019/0257912 A1* | 8/2019 | Remelius | G01S 3/782 |

OTHER PUBLICATIONS

Chatzitofis et al., "DeepMoCap: deep optical motion capture using multiple depth sensors and retro-reflectors", 2019 (Year: 2019).

\* cited by examiner

ACTIVE MARKER STROBING FOR PERFORMANCE CAPTURE COMMUNICATION

CROSS REFERENCES TO RELATED APPLICATIONS

This application claims priority from: U.S. Provisional Patent Application No. 62/983,523, entitled "Active Marker Device For Performance Capture," filed on Feb. 28, 2020; U.S. Provisional Patent Application No. 63/072,081, entitled "ACTIVE MARKER STROBING FOR PERFORMANCE CAPTURE COMMUNICATION" filed on Aug. 28, 2020; and U.S. Provisional Patent Application No. 63/072,082, entitled "STROBING BY ACTIVE MARKER GROUPS IN PERFORMANCE CAPTURE" filed on Aug. 28, 2020 which are hereby incorporated by reference as if set forth in full in this application for all purposes.

FIELD OF THE INVENTION

The present disclosure generally relates to visual productions and more particularly to detecting active markers in a live action scene for performance capture systems.

BACKGROUND

Visual productions often combine real and digital images to create animation and special effects. Such visual productions can include movies, videos, clips, and recorded visual media. Performance capture (or "motion capture") systems may be employed to obtain information about an actor on a location shoot, such as the person's shape, movement and facial expression. Data captured from light markers on the physical object in a live scene are used to create a computer-generated ("CG," "virtual," or "digital") character.

In performance capture, light from the markers are recorded to establish position, orientation, and/or movement of the object to which the markers are attached. Multiple markers are often employed that need to be distinguished from other markers and interfering lights in the scene. Data captured from the emitted light are analyzed to extract the desired information about the objects. Light from particular markers need to be distinguished from other markers. Light from the markers needs to be isolated from interfering non-marker lights on the set.

SUMMARY

Implementations of this application relate to light patterns used in a live action scene of a visual production to encode information about the markers, equipment associated with the markers, and/or the objects to which the markers are attached. For example, particular patterns of light strobing may convey a message as to which markers are attached to particular parts of objects. A data capture system is provided to recognize a group of active markers that emit light of a particular wavelength range for performance capture in a visual production. The present data capture system enables communication and coordination between the active markers and other components of the data capture system, e.g. a signal controller, a control unit for the active markers, and a performance capture system.

A method is provided for recognizing light from a group of active markers, in which a signal controller is synchronized with a capturing frame rate of one or more sensor devices of a performance capture system. The synchronization may include determining a reference time according to a time code that corresponds with a reference frame of the one or more sensor devices. Calibration signals may be sent from the signal controller to the group of active markers to emit calibration light based on the reference time. It may be determined whether the calibration light is received in one or more expected frames. Pattern signals are transmitted by the signal controller, to instruct the group of active markers to emit light of at least one wavelength range according to a pattern. According to the pattern, the presence of light coincides with one or more predefined illuminated frames and absence of the light coincides with one or more predefined blank frames of the performance capture system. One or more sensor devices of the performance capture system captures data representing the light in one or more illuminated frames and the absence of the light in one or more blank frames. The data is determined to be associated with the one or more illuminated frames and one or more blank frames correspond with the pattern in the one or more predefined illuminated frames and the one or more predefined blank frames. In this manner, the group of active markers is detected.

In some implementations, a phase locked loop may be used to synchronize the signals of the signal controller and the frame rate of the one or more sensor device. Based on the synchronizing, it may be determined that a sensor device is out of sync. The out of sync sensor device may be adjusted by one or more of realigning the out of sync sensor device, or reducing reprojection error to achieve predicted data collection. According to the synchronization, if it is determined that the calibration light from the active markers is out of sync with the reference time, the signals may be changed to alter the emitting of the calibration light in achieve synchronization.

In various implementations, it may be predicted for respective frames that the light is to be present or absent based on the pattern. The data capture system may confirm that the light is present or absent in the respective frames.

Some implementations synchronize the frame rate of the sensor device with a shutter action of a picture camera. The frame rate of the sensor device may be set to be faster than the shutter action of the picture camera, such that the pattern is detectable within a single cycle of the picture camera.

In various implementation of the method, a position of a first active marker of the group of active markers may be determined, and from the position, respective positions of other active markers of the group of active markers may be identified. At times, the active markers of the group of active markers may be configured to emit multiple wavelengths of the light. The pattern of the emitted light may include on and off intervals of light of uniform lengths.

A data capture system is also provided to recognize light from the group of active markers for the performance capture. The system may include a signal controller to transmit signals for the group of active markers to emit light of at least one wavelength range in a pattern. The pattern defines light to be emitted in on/off sequences in which presence of the light coincides with one or more illuminated predefined frames and absence of the light coincides with one or more predefined blank frames of a performance capture system. The signal controller may be synchronized with a frame rate of the performance capture system. The data capture system may further include the group of active markers to emit pulses of the light and at least one sensor device of the performance capture system to capture data representing the light and absence of the light from the group of active markers in respective one or more illuminated frames and one or more blank frames. The data capture system may further include a computing device to compare the data with the pattern and identify the group of active markers.

In some implementations, the signal controller and the performance capture system may be synchronized by determining a reference time according to a time code that corresponds with a reference frame of the sensor device. The group of active markers may be instructed by calibration signals of the signal controller to emit light based on the reference time.

The data capture system may further include a picture camera device having a shutter action that is synchronized with the frame rate of the at least one sensor device. The sensor device of the performance capture system may be set to be faster than the shutter action of the picture camera. The light pattern may be detectable within a single frame of the picture camera device.

The data capture system may also include a control unit in electrical communication with the group of active markers. The control unit may receive the signals from the signal controller and control the group of active markers to emit light according to the assigned pattern. In some implementations, a wired strand is coupled to the control unit and each active marker of the group of active markers for the purposes of electronic communication.

A non-transitory computer-readable storage medium may also be provided, such as in a computing device of the data capture system, that carries program instructions to recognize light from a group of active markers in performance capture associated with a visual production. The instructions when executed by one or more processors cause the one or more processors to perform operations that include synchronizing with a time code of a signal controller and performance capture system. The operations further include determining a pattern for the group of active markers to emit light of at least one wavelength range, in which presence of the light coincides with one or more predefined illuminated frames and absence of the light coincides with one or more predefined blank frames of the performance capture system. The operations also involve transmitting the pattern to the signal controller to instruct the group of active markers to emit the light according to the pattern. According to the operations, captured data is received from the performance capture system. The captured data represents the light in one or more illuminated frames and the absence of the light in one or more blank frames. Further to the operations, it is determined whether the captured data associated with the one or more illuminated frames and one or more blank frames correspond with the pattern in the one or more predefined illuminated frames and the one or more predefined blank frames. If the captured data is found to correspond with the pattern, the operations include identifying the group of active markers.

In some implementations of the computer-readable storage medium, the operations further include determining a reference time according to the time code and transmitting the reference time to the signal controller and performance capture system to synchronize the light with the reference time.

In some implementations, it may be determined that the one or more predefined illuminated frames and the one or more predefined blank frames lack the pattern. In these cases, the operations may include instructing the signal controller to adjust synchronization with the performance capture system. When the group of active markers is identified, the operations may include generating labels with the identified group of active markers by at least one of an object and part of the object to which the group of active markers is attached. Such labels and the captured data may be transmitted via the operations, to a computer graphics rendering system to be mapped to a virtual model.

In some implementations, the operations may be configured to receive status information from a control unit of the group of active markers and to provide a notification of the status information.

A further understanding of the nature and the advantages of particular embodiments disclosed herein may be realized by reference to the remaining portions of the specification and the attached drawings.

BRIEF DESCRIPTION OF THE DRAWINGS

Various embodiments in accordance with the present disclosure will be described with reference to the drawings.

FIGS. 6a and 6b are illustrations of various perspective views of an exemplary active marker strand, in which FIG. 6a is a marker coupled to a strand, and FIG. 6b is a side view of a receptacle housing the marker and strand, in accordance with some implementations.

FIGS. 7a and 7b are flowcharts of example methods for data capture of performance capture information in a live scene, in which FIG. 7a shows a method of synchronizing components of the data capture system and 7b shows a method of identifying active markers, in accordance with some implementations.

DETAILED DESCRIPTION

Figure 1:
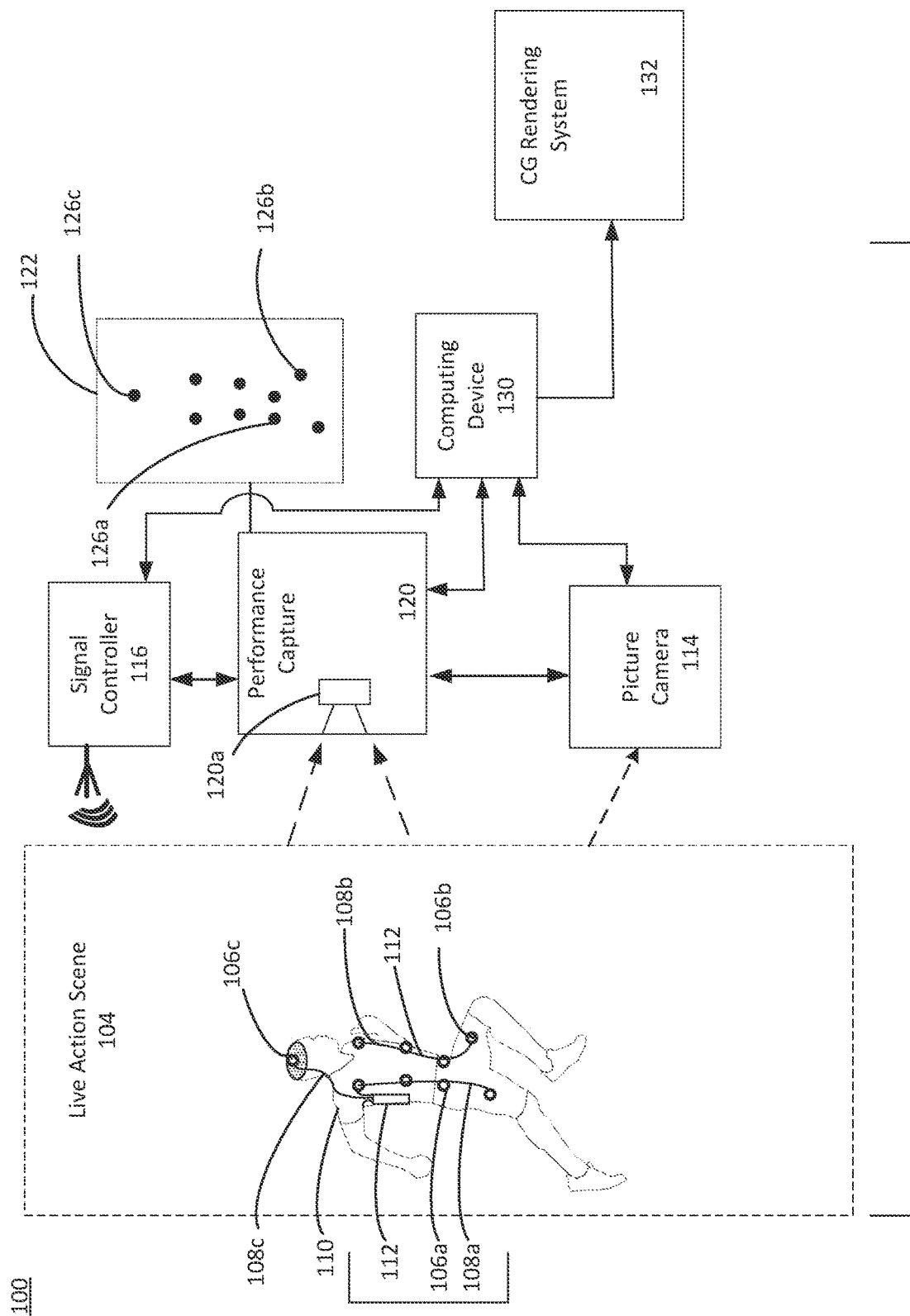
FIG. 1 is a conceptual block diagram illustrating an exemplary environment for capturing live action data for creating animation with a visual production system, in accordance with some implementations.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

The present data capture system employs active marker(s) that emit light of a particular wavelength range in predefined strobing patterns to communicate with a performance capture system and encode information associated with objects in the scene, such as movement and position of the objects. In some implementations, the active markers are instructed via a signal controller (also referred to as a synch signal controller) signaling a control unit, for the active markers to emit an assigned signature pattern of light. Timing of the signal controller is synchronized with a frame rate of sensor devices of the performance capture system. As a result of the synchronization, the pattern of emitted light corresponds with time slices including particular frames captured by the sensor devices. The frames include some that are illuminated and others that are blank in the assigned pattern. Frames showing the light pattern are analyzed to extract information about the active markers, such as identification of the active markers and objects to which they are attached.

Performance capture systems provide a valuable tool to generate data in a live action shoot for animation specialists to use. Live action shoots are typically expensive to run. Delays can add significantly to the overall cost of the production. It is desirable for the equipment used in performance capture to be easily adaptable to various shoots and enable quick and reliable processing of data.

Active markers are a type of marker that emits light of specific wavelengths, e.g. infrared, detectable by particular camera devices. In one animation technique, the information gathered from active marker detection is processed and mapped to a 3-D model to create a CG representation. As described in greater detail later in this description, the light emitted by the active marker may be any frequency of electromagnetic radiation. For example, a particular wavelength range of light may be selected within various types of non-visible light and visible light, such as infrared, ultraviolet radiation, etc.

In visual productions, objects in a live action scene that are to be converted to animated versions of the objects may have attached active markers. Often, numerous active markers are employed across various objects and the emitted light is captured by multiple camera sensors. Sorting the data and extracting information from the light patches captured in the frames may be time consuming and prone to errors. Rather than using software processing to determine which active marker light is being captured, the present data capture system employs hardware controls to synchronize and control light emitted in patterns to predict capturing of light within predefined frames. In this manner, light detection from active makers is more efficient by the system knowing what is to be captured at any moment.

For illustration purposes of one example, a visual production using traditional performance capture technology may have a hero actor riding on top of a tank vehicle. The hero actor is to be animated and has a total of 48 active markers on various parts of its clothing, headwear, gloves, and shoes. The active markers in this example of traditional technology may emit constant light.

The imagery data captured by this traditional performance capture system consist of spots of light that are difficult to differentiate from each other. There may be additional actors also riding in the tank with active markers. It would be time consuming to reconstruct objects by spatial location alone and determine which light spots are from the hero actor. There can be multitudinous combinations of spatial arrangements to figure out for each marker when processing the data from scratch. Furthermore, some of the captured spots may erroneously thought to be an active marker light, but may be from interfering light sources in the same frequency range as the active marker light, such as sunlight or other devices that provide a source of continuous light on the production set.

The present data capture system addresses these drawbacks and provides for reliability and simplicity in extracting information from light emitted from active markers. Use of predictable light patterns enables the system to filter out interfering lights. The active markers with the light pattern may be localized on an object, such as the hero actor in the previous example. Pulsing of light further reduces energy requirements and battery life as compared to constant light. In some implementations, once one active marker or group of active markers is identified, the data capture system may measure a spatial position from the identified active marker to the other markers on the object.

To further simplify detection of active markers, devices of the data capture system may be synchronized in time, leading to predicable frames within distinct time slices that depict the predefined light pattern. For example, the active marker groups and performance capture camera may be synchronized according to a time code. The computing device and software running on the computing device may also be synchronized with the time code. In this manner, changing the frame rates of devices may not affect the devices working in sync. The sensor devices and active markers may further operate at a same rate, avoiding a need for dedicated sensor device with particular CCD's configured for a particular active marker. The flexibility of devices to detect groups of active marker allows a production team to easily switch cameras as the actor moves around the live scene.

Synchronization of sensor devices enable adjusting of a sensor device that is found to be out of synch based on knowledge of what data is supposed to be captured for any given group of active markers. The out of synch sensor device may be adjusted by realigning the sensor device and/or reducing or otherwise minimizing reprojection error. Whereas previous systems may only adjust for minor drift, the present data capture system may enable significant readjustment of a sensor device to achieve the predicted data collection.

In traditional systems, signals from a transmitter may also get mixed with interfering signals, e.g. environmental signals or signals from other devices in the same or similar frequency. The present data capture system may address this drawback by a signal controller providing key sequence signals for the active markers to zone in on the pattern command signals. The key sequence signals may be transmitted prior to and/or after the pattern signals for various active markers. An initial key sequence may be used to inform the control unit for the active markers that the signature pattern signals are being transmitted subsequent to the initial key sequence. A terminal key sequence informs the control unit ending of the signature pattern signals.

Other benefits of the present data capture system will be apparent from the further description of the system, as described below.

Various components of a visual production system include: (1) live action components such as the present data capture system for generating visual data from a scene including the described performance capture system, active markers, signal controller, and picture camera(s); (2) virtual production components for generating CG graphic information based on the visual data; and (3) content compositing components for generating output images. Any of the system components may communicate with the other components through a network, radio frequency signals, or other data transfer technologies.

FIG. 1 is a block diagram of an example environment for capturing live action data for creating animation with a visual production system 100, as described herein. The visual production system 100 is a representation of various computing resources that can be used to perform the process actions and steps described herein. Any number and type of discrete or integrated hardware and software components, such as program instructions carried in a non-transitory computer readable storage medium, may be used to perform the methods described. The components may be located local to, or remote from the other system components, for example, interlinked by one or more networks, radio frequency communication, etc.

The live action scene 104 defines the space available for recording and may include a motion production set, a performing stage, an event or activity, a natural outdoor environment, etc. Implementations of a data capture system 102 includes a performance capture system 120 to detect light diffused from active markers 112 in the live action scene 104 and generate marker data 122, a signal controller 116 to send instructions that direct the active marker 112, a picture camera 114 to capture visual data from the live action scene 104, and a computing device 130 to define light patterns and analyze the various captured data. During a pre-capture phase, the components of the data capture system 102 are synchronized in time, e.g. by a time code, for coordinated data capture, as described in detail later in this description.

Software may be used to define a signature pattern for a particular group of active markers, for example, by computing device 130. The signature pattern is based on a time code and frame rate of the sensor devices, e.g., dedicated cameras, of the performance capture system 120. The signature pattern dictates particular frames within specific time slices that are to be exposed with light (referred to as illuminated frames) and frames that are to be unexposed (referred to as blank frames). Thus, the pattern includes timing elements so that the control unit may time the powering of active markers and the light will be emitted in particular time slots of the sensor device of the performance capture system. The signature pattern determines duration of light pulses and gap periods between light pulses by active markers. Typically, the amplitude or intensity of light remains constant. In various implementations, the pattern provides for light to be emitted when a capture device shutter is open and no light is to be emitted when the capture device shutter is closed. In some implementations, the duration of light pulses is uniform, such that intensity variations are not factors in the detection of the signature pattern.

The signal controller 116 receives pattern information that define the pattern including timing of the light pulses, e.g. from the computing device, for any given group of active markers. The signal controller encodes and converts the digital pattern data to analog signals. The signal controller may amplify the signal to a higher power level and feeds the signals to an antenna for transmission in the form of electromagnetic waves in the air. In some implementations, the signal controller 116 may include a radio frequency transmitter that transmits radio frequency waveform signals. However, other forms of data transmission are possible, such as IR transmission. In still some implementations, a light pattern may be set at the control unit 112 and the data capture system 102 may not require a signal controller 116 to convey the light pattern to the control unit 112.

The active markers may be placed in the live action scene at a distance that enables receiving of signals by the active marker from the signal controller 116 and detection of light from the active marker by the performance capture system 120. For example, the active marker may be located up to 50 m from the signal controller 116.

A control unit 112 of the active marker apparatus 112, worn on the actor 110 includes a receiver to collect the signals from the air via an antenna. As there may be many types of electromagnetic waves in the air, the control unit filters out the desired signal. The signal may be amplified and fed to the analog to digital converter, which converts the analog signal to digital signal. These digital signals may be demodulated and pattern information decoded. The control unit regulates the groups of active markers (106a, 106b, 106c) to emit light according to the pattern information. For example, the control unit may transfer electrical power in pulses in line with the pattern, to the active markers through wired strands (108a, 108b, 108c) that connect groups of active markers (106a, 106b, 106c).

Shown in FIG. 1, are three groups of active markers coupled to individual strands: four active markers 106a attached to the right front torso of the actor and coupled to strand 108a, four active markers 106b attached to the left front torso of the actor and coupled to strand 108b, and a single active marker 106c attached to the head of the actor and coupled to strand 108c. Each active marker within a group operates at a same frame rate according to the signature pattern assigned to the group.

The actor 110 may have any number of groups coupled to one or more control units 112. Groups of active markers include at least one active marker, such as two or more active markers, e.g. 2-8 active markers. For example, each group may consist of eight (8) markers, each coupled to a strand. The actor may have eight (8) groups extending to various parts of the actor 110. Although an actor is depicted in FIG. 1 for illustration purposes, the active markers may be attached to various types of live or inanimate objects in the live action scene 104, such as props, animals, cameras, other actors, etc. In some implementations, the active markers may be held by receptacles that attach the active markers to the object. Stands may be positioned underneath or on top of a wearable article. In some implementations, some active marker may be positioned directly on the person 110, such as with adhesive, rather than a wearable article.

In various implementations, the strand 108 may include wires that run inside the length of a flexible tube or sleeve, e.g. in a conduit in the strand, heat shrink tubing, protective wrap or tape, coating over the wires, etc. Other forms of the strand may be possible for wired communication to and/or from active markers, e.g. to control pulsing of light be the active marker via a control unit. In some implementations, the strand may be one or more wires, e.g. bare wires, embedded within a protective material of the wearable article.

In some implementations, wireless active markers may be employed that are independently controlled with an on-board input/output interface to receive wireless sync signals via a wireless format, such as from signal controller 116 and/or control unit 112. The wireless active marker may also include logic. In these implementations, the active markers may not employ a strand for electronical control of the active markers. In some implementations, wireless active markers with on-board receivers communicate directly with the signal controller 116 without the need for the control unit 112.

In various implementations, all active markers in a group, such as active markers coupled to a strand and positioned in an area of an object, may emit a same pattern. In some implementations, different groups on a same object or groups on different objects may each emit distinctive signature patterns of light to which each are assigned. Identification of one reference active marker or one reference group of active markers may allow the data capture system to identify other markers. The computing device 130 may determine and/or include prior knowledge of spatial relationships among the active markers relative to each other. Such knowledge may be used in identifying markers based on detecting light patterns from other groups of active markers. Such grouping of active markers may provide advantages over needing to identify each marker by its own pattern. For example, individual marker tracking may require excessive resources to detect and analyze each marker.

The light source of the active marker (106a, 106b, 106c) may be infrared LED, e.g. between 700 nm and 1 mm, or more specifically between 800 nm and 960 nm. For example, the light source can be a 940 nm wavelength, 1 watt infrared (IR) LED. However, other light sources are possible, such as ultraviolet light source and the sensor device is an ultraviolet detector. In some implementations, various wattage light sources may be employed depending on the live scene of the shoot. For example, higher wattage may be used when shooting in bright daylight and lesser wattage for dark scenes.

In some implementations, a different wavelength of light or filters, or combinations of different wavelengths may be used for various different markers in a scene or at certain times during a shoot. In some implementations, varying of wavelengths of light may enable further communication by the active markers for detection. For example, active markers may strobe a change in wavelength to indicate low battery power or other events that require attention. Different groups of active markers may strobe particular different wavelengths to further indicate its location in a scene or the object bearing the active markers. In this manner, various information in addition to identification of the active markers, may be encoded in the sequences and patterns of light being emitted by the active markers.

Furthermore, varying the wavelength of light by active markers may facilitate detection under various conditions that favor a certain wavelength, such as fog, and based on a resolution and optical contrast required to produce the data needed by the CG rendering system 126 for animation. For example, active markers that emit blue wavelength light may be used for water settings. In some implementations, specialized environmental sensors within components of the data capture system, e.g. the control unit and the signal controller, may detect a change in environment that necessitates a different light wavelength. In response, the active markers may be instructed to change the light accordingly. In situations where wavelengths of light vary, the performance capture system may include sensors that filter for the various wavelengths of light.

The performance capture system 120 may include any number of sensor devices 120a to detect the light emitted from the active markers. The sensor device 120a may include a narrow-pass filter to detect a particular wavelength or range of wavelengths of the light emitted from the active markers. In some implementations, the sensor device 120a may be configured to detect multiple distinct wavelengths of light. For example, a sensor device may include filters to separately detect different wavelengths in an infrared range, or machine vision cameras for ultraviolet wavelengths. In some implementations, multiple sensor devices may be employed with individual sensor devices being dedicated to a wavelength of light.

In some implementations, the sensor device 120a may be a global shutter CCD sensor. In some implementations, one or more sensor devices 120a of the performance capture system 120 may include a visible light filter to block visible light and allow only particular wavelengths, e.g. short wavelength infrared light, to be detected by the camera sensor. Various cameras may be used by the performance capture systems, such as a computer vision camera and mono camera that is sensitive to infrared light (700 nm to 1 mm wavelength light), e.g., that exclude infrared blocking filters.

In some implementations, different sensor devices (e.g. cameras) may be devoted to particular wavelengths of light from different active markers. In some implementations, a sensor device of the performance capture system may include stacked filters that may be rotated or otherwise swapped, into place depending on the particular wavelength to be detected at any given moment. The performance capture system configured to capture alternating wavelengths of light enables encoding of more information based on the wavelength emitted. Swapping sensor filters isolates the particular wavelength being emitted at any given time. For example, filters may enable separation and detection of short infrared light, e.g. 950-1000 nm wavelength, special sensors heat-type filters may be used for long wave infrared, other filters may be used to detect 700-1000 nm wavelength light, and 280-650 nm visible light.

In some implementations, the sensor device(s) 120a may include one or more time of flight sensors to detect time of flight of the light. The time of flight sensors may infer position and volume of the light by multiple sensor devices detecting an arrival of the light at the respective sensor devices at different times. In determining an arrival time, such time of flight sensors may use an emittance time in which the active marker light is expected to emit light, as predetermined and directed by signals from the controller. The light data may be represented in three-dimensional (3-D) images. The capturing of light in "frames", such as illuminated frames, refers to time periods in which light arrives and is detected at the individual sensor devices. Accordingly, blank frames refer to time periods in which light is determined not to be present.

A picture camera 114 captures visible light of the live action scene 104, viewable by an observer such as the objects. In some implementations, the picture camera 114 may also capture data to assist in identification of the active markers, such as a color and/or shape of receptacles holding the active markers. In some implementations, the picture camera 114 and performance capture camera may be synchronized. Data from the picture camera 114 and the performance capture camera may be combined to determine a marker arrangement 122.

The computing device 130 of the data capture system determines the marker arrangement 122 from data 124 representing positions of the detected markers. The marker data from the picture camera may also be used to match CG parameters for CG images with picture camera parameters, such as perspective, position, focal length, aperture, and magnification, of the CG images. In this manner the CG images may be created in an appropriate spatial relationship with the live action objects.

The computing device 130, via software running on the computing device, may further label the object and/or part of the object to which the group of active markers are attached. The computing device 130, via software running on the computing device, feeds marker data and/or object labels obtained from the detection of the active markers to the CG (computer graphics) rendering system 132 to be mapped to a virtual model using software of the CG rendering system 132. The CG rendering system 132 may represent the data in a virtual environment. For example, computer programs may be used by CG rendering system 132 to overlay information on top of movements of the actor 110 represented by the data.

The CG rendering system 132 may include computer processing capabilities, image processing capabilities, one or more processors, program code storage for storing program instructions executable by the one or more processors, as well as user input devices and user output devices (e.g., animation and rendering components of system 1000 described below with regard to FIGS. 9 and 10).

Figure 2:
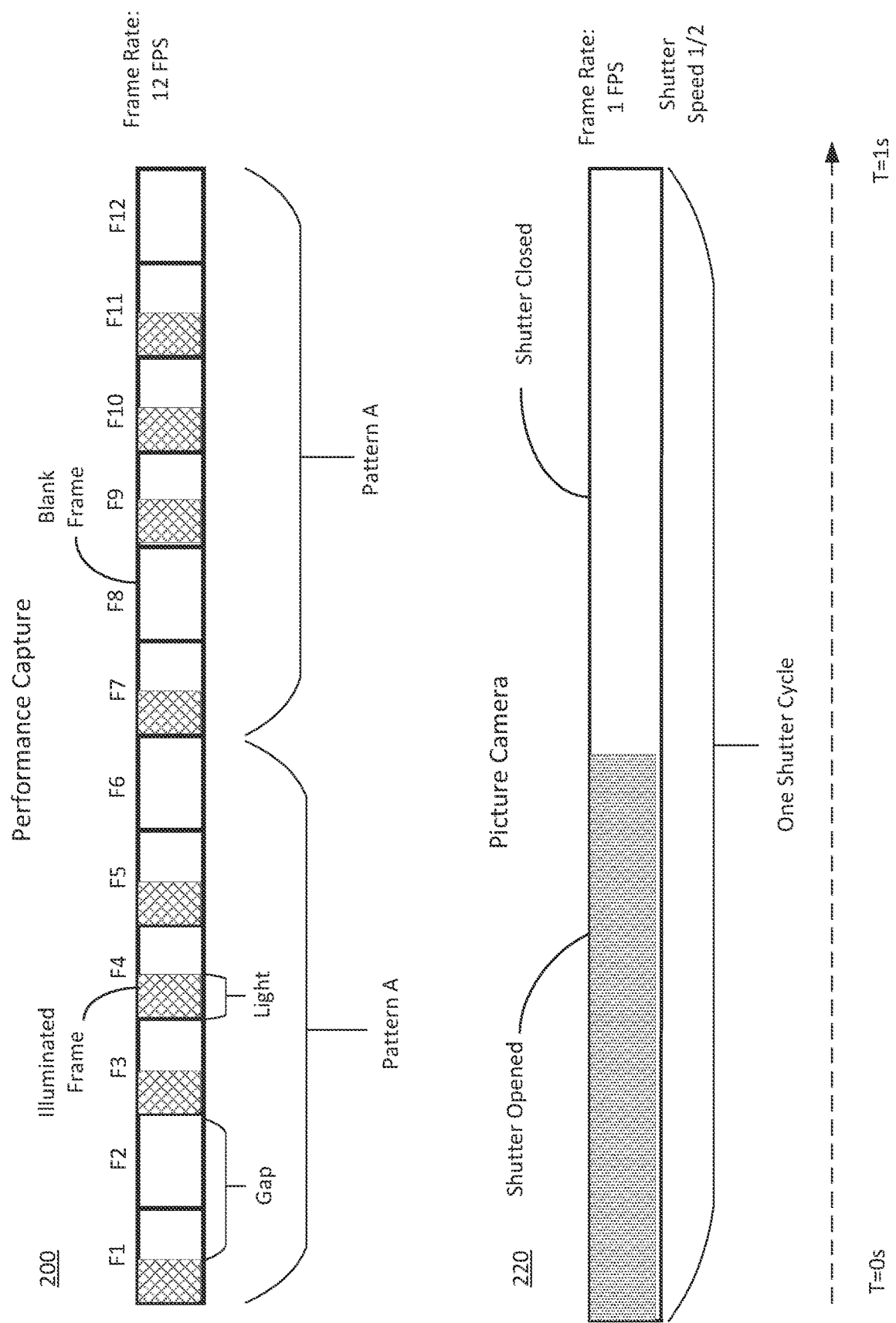
FIG. 2 is an illustration of example captured frames and rates of a performance capture device and picture camera, in accordance with some implementations.

FIG. 2 illustrates exemplary frames 200 within time slices of a video captured by a sensor device of the performance capture system (e.g. 120 in FIG. 1) and frames 220 within time slices of a video captured by a picture camera (e.g. 114 in FIG. 1), during a one second period of time. A time slice for the sensor device and picture camera is a period time in which an image is captured and includes the time between frames before the next frame is captured. In some implementations, a sensor device of the performance capture system may capture at a higher frame rate than the picture camera frame rate such that the signature pattern of light emitted from the active markers is detectable within a portion of a single cycle of the picture camera.

For simplicity in the illustration shown in FIG. 2, the performance capture device captures at a rate of 12 frames per second (fps) and the picture camera captures at a rate of 1 fps. In practice, the picture camera may shoot at various frame rates, such as 24 frames per second. The sensor device may also capture at various frame rates, such as 60 fps or 120 fps. In some implementations, the sensor device may run at a higher rate than the camera rate, e.g., 5 times the picture camera rate, such as 120 fps with a picture camera rate of 24 fps. The sensor device may run at such as high rate that a light pattern is virtually unnoticeable in the frames of the picture camera. For example, a user observing the scene may merely witness flickers of light or a seemingly continuous light source.

Pattern "A" consists of light periods and gap periods in which there is no light emitted between the light periods. This results in individual frames of the performance capture system including illuminated frames in which light is detected from the active markers and blank frames in which no light is detected and it is determined that no light is present or emitted by an active marker. Pattern A, for example, includes an illuminated frame F1, blank frame F2, followed by three illuminated frames F3, F4, and F5, and ending with blank frame F6.

A single instance of the pattern can cover any distinguishable number of frames of the performance capture device sensor. In FIG. 2, the Pattern "A" is 6 (six) performance capture frames long and is repeated twice within a second of a video. Using a single pattern instance that encompasses a larger number of frames of the performance capture sensor device, enables exponentially greater number of combinations for the pattern. For example, a 5 frame pattern enables 32 distinguishable patterns to choose from for a given group of active markers. An 8 frame pattern allows for 256 different combinations. However, longer patterns may also increase the complexity of pattern and time for detection.

Further to the example in FIG. 2, a single time slice of the picture camera is shown with a shutter action speed of ½. The shutter is open for ½ of a second, which is half the duration of each shutter cycle of the picture camera. The shutter action of the picture camera includes opening and closing of the shutter during capture. A single cycle is made up of the capture period in which the picture camera is capturing while the shutter is open and the closed period when the camera is not capturing while the shutter is shut before the next frame begins.

In some implementations, the light pattern is detectable by the sensor device of the performance capture system within a single cycle of the picture camera. In the example shown, the performance capture device may detect two repetitions of Pattern A within a single cycle of the picture camera.

Figure 3:
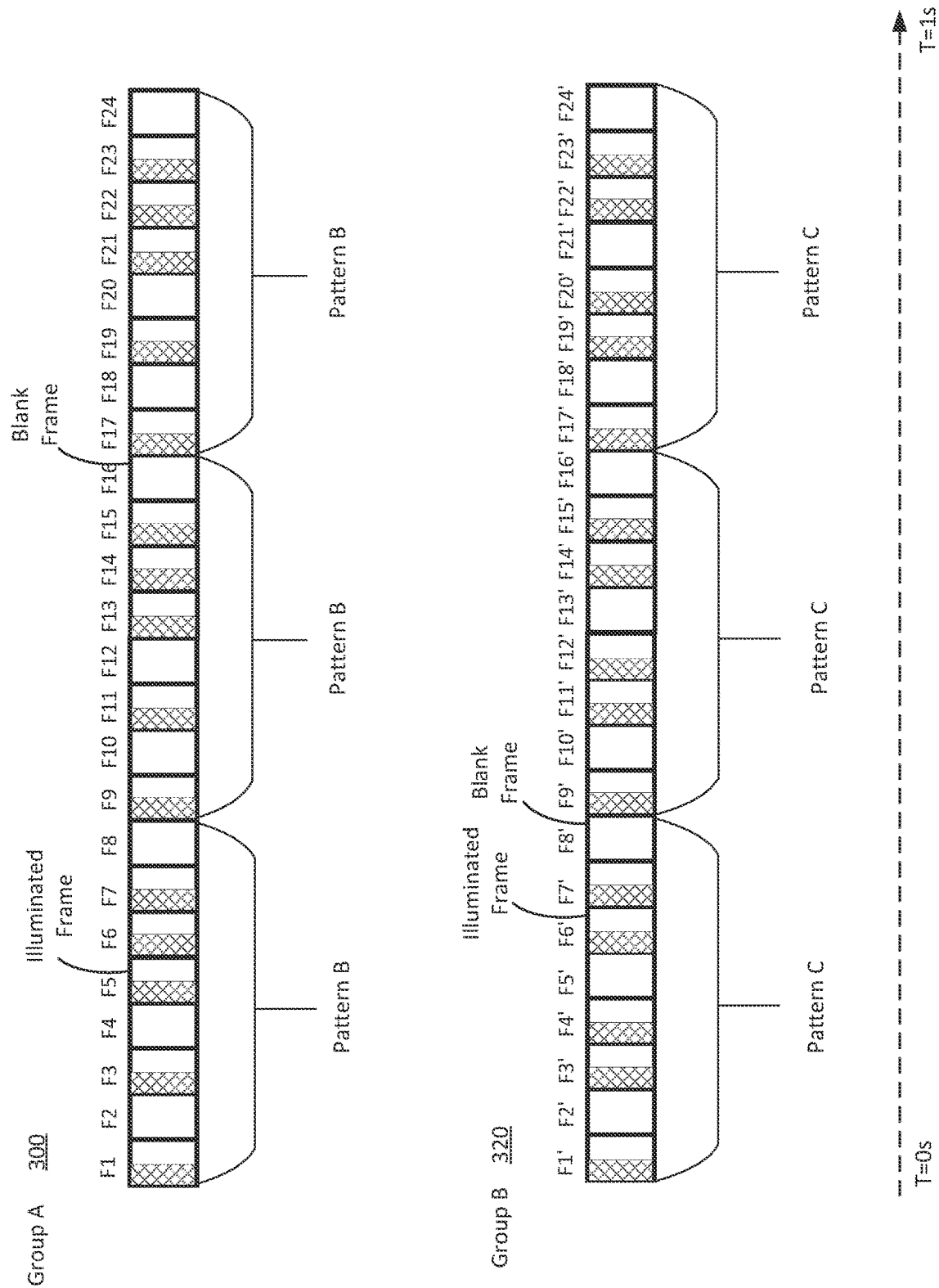
FIG. 3 is an illustration of exemplary captured frames with light patterns from groups of active markers, in accordance with some implementations.

In some implementations, multiple groups of active markers may be assigned to different signature patterns to enable the data capture system to distinguish between groups. FIG. 3 illustrates an example of two sets of captured frames depicting light patterns from groups of active markers, Group A and Group B. At a frame rate of 24 fps, the performance capture system may capture three repetitions of the signature patterns in one second. Active markers in Group A 300 emit light to illuminate frames according to Pattern "B", which consists of an 8 (eight) frame pattern. Pattern "B" includes an illuminated first frame F1, blank second frame F2, illuminated next frame F3, followed by blank frame F4, three illuminated sequential frames F5, F6, F7, and blank frame F8.

Active markers in Group B 320 emit light to illuminate frames according to Pattern "C", which consists of an 8 frame pattern. Pattern "C" includes an illuminated first frame F1', blank second frame F2', two illuminated sequential frames F3' and F4', followed by blank frame F5', two illuminated sequential frames F6' and F7' and blank frame F8'.

In some implementation, a key sequence may be used in conjunction with the pattern signals. The key sequence may be a code sent by the signal controller 116 to isolate the pattern signal for a given group of active markers 108. The control unit may be programmed to detect the key sequence and ignore other interference signals in the same or similar frequency of the signal controller 116.

The key sequence may be used to define a group and its pattern signals and for different groups to separate their assigned signature patterns. For example, two or more groups of active markers may be assigned respective signature light patterns with different key sequence for each group. A control unit may be programmed to recognize different particular key sequences as assigned to particular groups of active markers under the control unit's control. The control unit may receive an initial key sequence for a particular group, which triggers the control unit to apply the pattern signals that follows to the particular group.

The computing device 130, via software running on the computing device, may determine the key sequences for various groups of active markers. In some implementations, various control units may be programmed to recognize the initial and/or terminal key sequences assigned to various groups under the respective control units' control. In this manner, different control units may be activated under particular initial key sequences. The terminal key sequence may indicate to the control unit that the pattern signals have ended. In some implementations, the terminal key sequence may indicate to the control unit to prepare to detect another initial key sequence for other pattern signals intended for another group of active markers.

Key sequences, initial calibration key sequences and terminal calibration key sequences, may also be employed to signify calibration signals during synchronization of components. Thus, various groups of active markers may be sequentially triggered during synchronization to determine accuracy in timing of the light from the various groups.

In various implementations, additional signals may be inserted to provide additional commands or information. For example, extra signals may be inserted prior to the initial key sequence or between the initial key sequence and the pattern signals. Likewise, extra signals may be inserted between the pattern signals and the terminal key sequence or after the terminal key sequence. In other implementations, the initial key sequence immediately precedes the pattern signals and the terminal key sequence immediately follows the pattern signals, with no extra signals in between.

Figure 4:
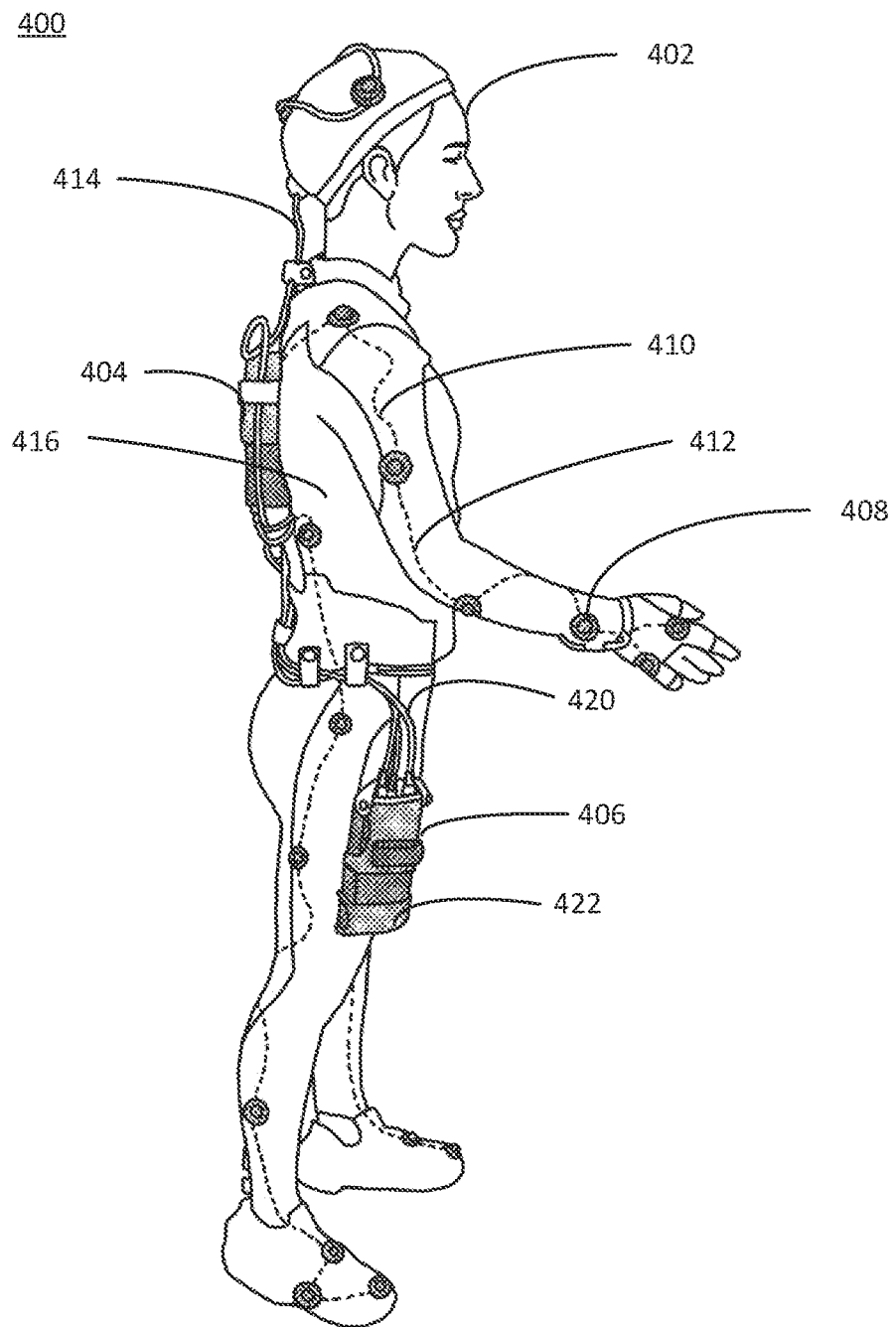
FIG. 4 is a side perspective view diagram of an actor wearing a control unit including a main pack and transceiver, in accordance with some implementations.

FIG. 4 is a side perspective view diagram of an actor 402 wearing a control unit 400 that includes a main pack 404 and transceiver 406, which may be used for implementations described herein. In various implementations, control unit 400 receives external signals (calibration signals, pattern signals, key sequences, clock signals, etc.) via transceiver 406 and electrically communicates to active markers 408 through wired strands 410. The strands 410 may include internal strands 412 (or strand portions) that are channeled underneath a wearable article 416, and external strands 414 (or strand portions) that are strung outside of the wearable article 416.

The transceiver 406 includes an antenna to receive signals, e.g. from the signal controller. The transceiver 406 may further include one or more cables 420, which may include output cables and input cables to couple the transceiver 406 to the main pack 404. For example, the receiver may receive analog signals in the form of radio frequency signals and transfer the analog signals through output cables 420 to the main pack 404 for conversion to digital signals. In some implementations, the transceiver may receive power through cables 420 from a battery in the main pack 404 or the transceiver may include its own internal power source.

In some implementations, the transceiver 406 may include input cable 420 to receive data from the main pack 404 and transmit the data, e.g. radio frequency signals, to other components of the data capture system, such as the sync controller (116 in FIG. 1), the performance capture system (129 in FIG. 1) and/or the computing device (130 in FIG. 1). For example, main pack 404 may provide the transceiver 406 with status information that a power source is low, a component of the control unit is malfunctioning, e.g. onboard computing device, a particular strand or active marker, etc., or other such information needing attention. In some implementations, status information may be sent via transceiver 406 to confirm proper operation of the control unit, e.g. during an operation check. In some implementations, the computing device (e.g. 130 in FIG. 1, via software running on the computing device) receives the status information and outputs a notification of the status, such as an audio indicator, visual display indicator, etc. Other information sent by the transceiver 406 is possible.

If an active marker on a strand group becomes inoperable, the entire strand may go down. In some implementations, the control unit may detect operation problems with a strand not pulling expected power and resulting in voltage changes. The control unit may communicate problems back to the performance capture system via the transceiver sending an alert notification that may include an identification of the malfunctioning strand. In some implementations, the control unit may send periodic reports on the strand operations on a regular interval, such as one second pulses.

In various implementations, instead of the transceiver, the control unit may include a separate receiver and transmitter. In still some implementations, the control unit may only include a receiver and not a transmitter.

The transceiver 406 may be secured to the wearable article 416 by a pouch 422, straps, snaps, zippers, etc. In some implementations, the pouch 422 may be removable to relocate the transceiver 406 to other locations on the object. Various zippers and fasteners may be adjusted as needed. The transceiver and main pack may be detached from the wearable article 416 and strands 412, such as for maintenance, replacement, etc.

Figure 5:
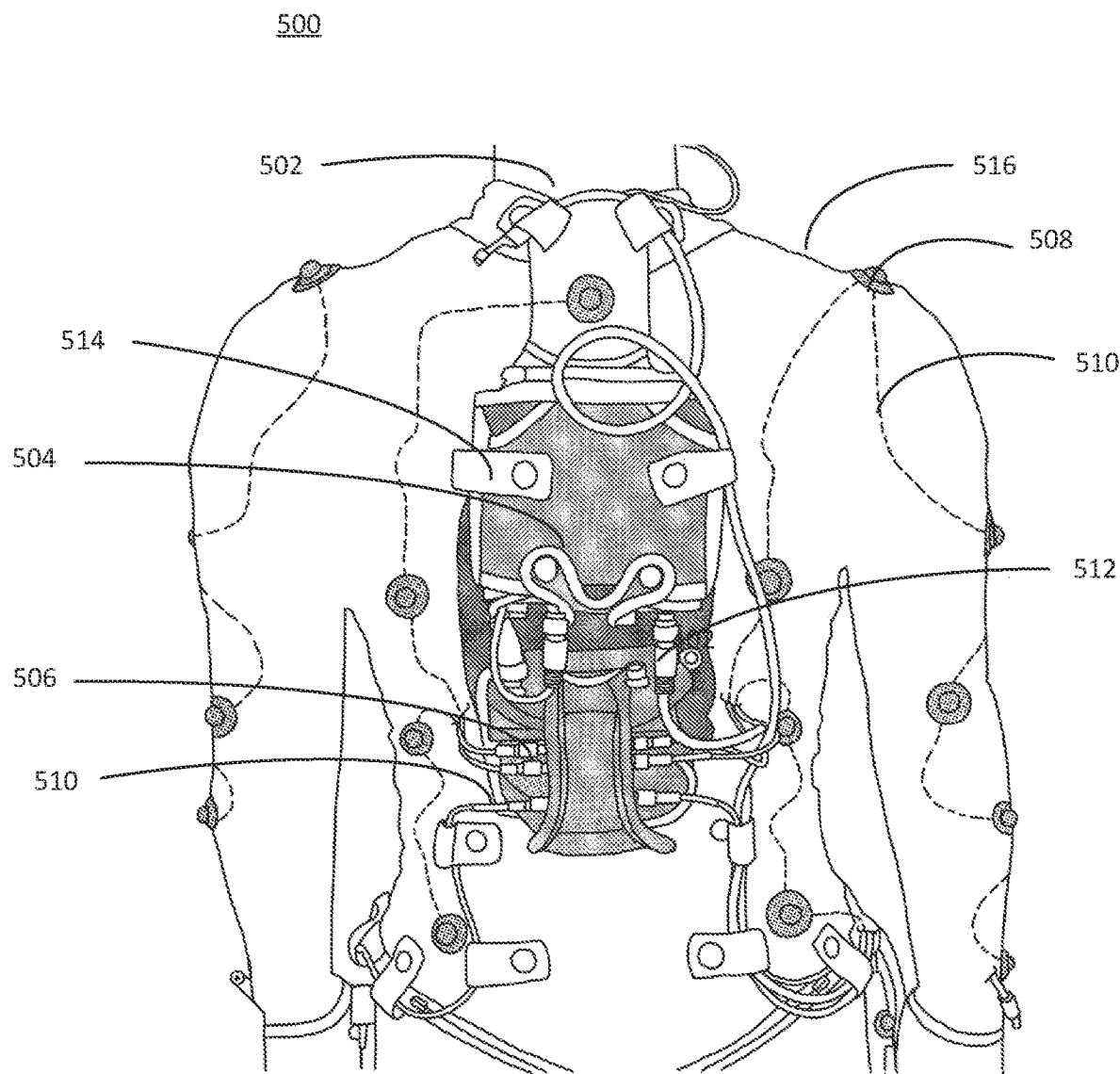
FIG. 5 is a rear perspective view diagram of an actor wearing a main pack of a control unit on the back of the actor, in accordance with some implementations.

FIG. 5 shows an example of a main pack 504 of the control unit 500 on the back of an actor 502. The main pack 504 includes multiple strand connectors 506 to couple strands 510 to the main pack 504 and to communicate with active markers 508. The example in FIG. 5 shows six strand connectors 506 attached to six strands of active markers extending to various parts of the actor 502 from the main pack 504. The main pack 504 further includes one or more transceiver connectors 512 to couple one or more cables to the transceiver.

In some implementations, the main pack 504 may include also include an onboard computing device with logic to perform various functions, such as copy a clock signal, interpret light pattern information from the received pattern signals, identify key sequences, turn markers on and off, read battery status, set brightness levels, detect issues with the markers, record data, etc. In some implementations the main pack 504 may include recording mechanisms to record active marker data, such as facial data. Such data may be transmitted to the data capture system via the transceiver.

The main pack 504 may include a power source, such as a battery unit, to supply power to the main pack and various other components, such as the active markers and the transceiver. The power source may be replaced as needed when the energy runs low by detaching from the strands and wearable article, without the object, e.g., actor, needing to remove the wearable article. For example, the power source may last about 2 to 6 hours, such as about 5 hours. Various types of batteries may be employed with different capacities. In some implementations, the main pack may have dedicated power supplies for each strand or for collections of strands.

The main pack 504 may further include other components for using signals received through the transceiver and to send data through the transceiver, such as an analog to digital converter, amplifier, modulator, etc. The main pack 504 may be secured to the actor 502 through various fasteners 514, such as snaps, straps, a pouch in the wearable article 516, zippers, etc.

Figure 6A:
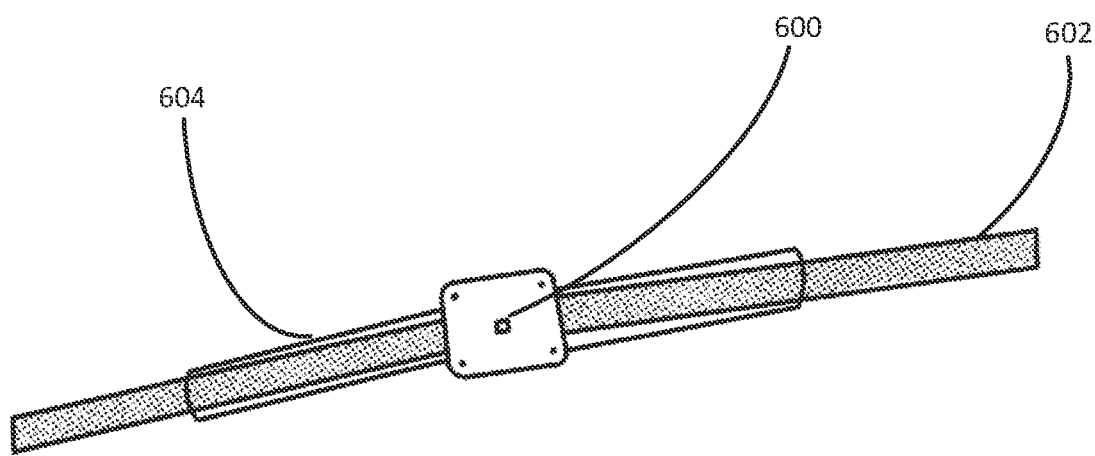

As shown in FIG. 6a, an active marker 600 may be coupled to a strand 602. A protective covering 604, e.g. heat shrink tubing, may cover internal wires at the area that the active marker is attached to the strand and the general area of the receptacle once the active marker is inserted into the receptacle. The protective covering 604 may be provided to insulate, protect and seal the active marker 600 with the strand 602. The strand 602 may be a flexible material. The strand may contain a wire or be a naked wire. The wire typically includes a highly conductive element, such as copper, silver, gold, or aluminum, and may be uncoiled, stranded, solid, braided, etc. The strand provides a pathway for electronic communication between various components of the data capture components on the object. For example, the strand may be a conduit of electrical signals between components, such as from/to one or more control units and active markers, between the active markers within a group, and/or between groups of active markers with other groups of active markers.

The active marker 600 may include one or more light sources, such as an LED or an array of a plurality of LED's (e.g. a bundle of three LED's). A group of a plurality of active markers 600 may be coupled to the strand 602, such as 2 to 15, for example, 8 active markers on a strand.

Figure 6B:
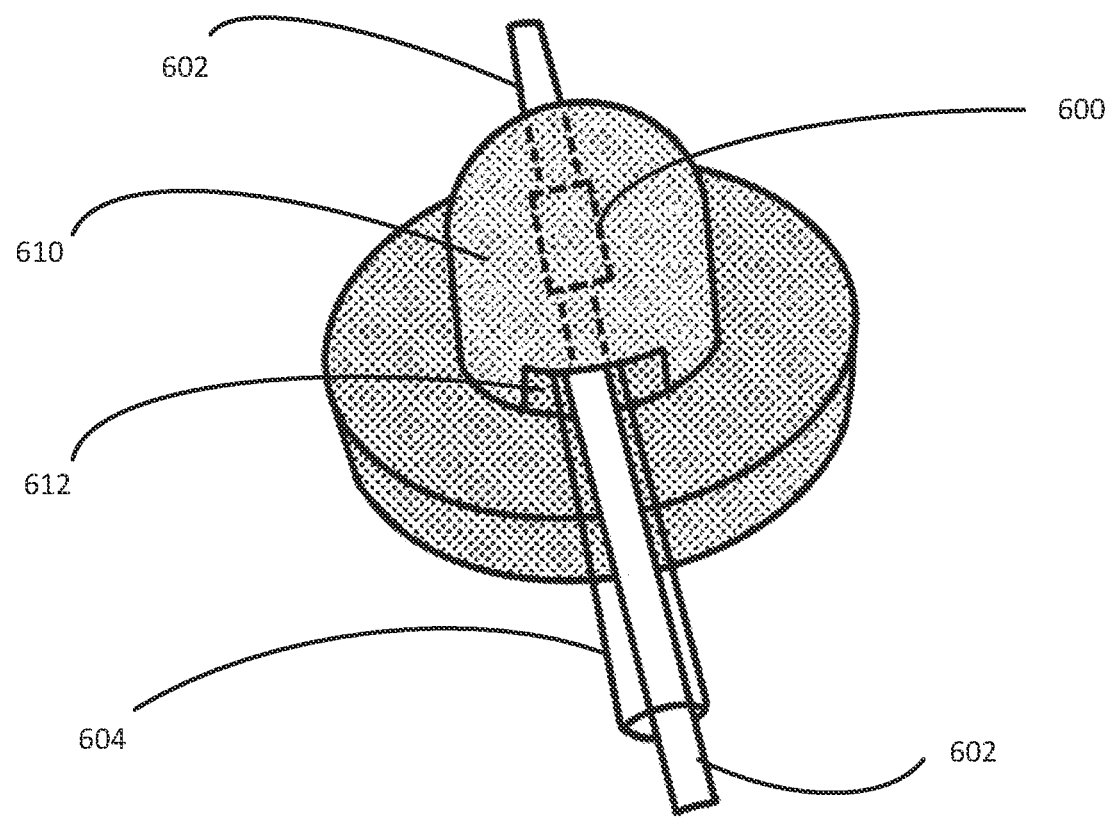

As shown in FIG. 6b, an active marker 600 that is coupled to strand 602 may be housed in receptacle 610. In some implementations the active marker 600 and strand 602 may be fitted within the receptacle 610 by inserting into slot 612 of the receptacle 610. Once inserted, the strand 602 may be positioned to extend from an entrance port of the receptacle 610 and further extended through an exit port out of the receptacle 610. The protective tubing 604 may extend from the active marker 600 to a portion of the strand outside of the receptacle 610.

The process of recognizing light from active markers in performance capture may include a pre-capture phase and a capture phase. As shown by the flowchart in FIG. 7a, the pre-capture phase 700 includes synchronizing various device components, such as the signal controller, sensor devices of the performance capture system, active marker control units and picture cameras, of the data capture system of the visual production system.

In block 702, a reference time point is determined by a time code, for example via computing device 130 in FIG. 1. The time code, such as Society of Motion Picture and Television Engineers (SMPTE) time code, may be used as a universal time to coordination the signal actions of the signal controller, the frame rate of the performance capture system sensor devices, the control actions of the control unit for the active markers, and/or the picture camera frame rate. In some implementations, the devices, such as the image capture device, depth cameras, performance capture system, etc., may be synced by a phase locked loop of the signals of the devices and the timing maintained with a timing reference block or a wired genlock source A phase lock device may be used for wireless syncing of the timing and other parameters of camera devices by generating a reference block. For example, the phase lock device may take large sample sizes, such as 1000 samples, to adjust parameters, such as the phase, time code, broadcast sync standard, through the lens (TTL) metering, performing at rate or a multiplier of the rate (e.g., 24 fps and 24 fps timecode). The copy of the reference signal may be used to calibrate other devices based on the reference block. For example, a device may be calibrated at a multiple of the rate of the reference block, e.g. twice the speed of the reference block, synchronize to the same speed or time code as the reference block, to a square wave, etc.

In block 704 the signal controller transmits calibration signals to the active marker control unit intended for a particular group of active markers based on the reference time point. In block 706, light response by the active markers is regulated by the control unit.

The light response is observed in captured frames by the sensor devices of the performance capture device. In block 708, one or more sensor devices of the performance capture system captures light response in frame(s). The particular group emits light or turns off light at the reference time point according to control unit having received the calibration signals. For example, where the group of active markers includes all markers on a given strand on an object, or all active markers on the object that may be switched on and off by the control unit.

In decision block 710, it is determined whether the light response in the predefined calibration frames is in the intended frames? It is determined whether the particular group is emitting light or turning off light at predefined frame of the reference time point. If the light is out of sync with the reference time point, the devices may be adjusted. In block 712, the calibration signals, the sensor device, and/or the control unit are adjusted. For example, the signals may be varied or the control unit timing modified to adjust the emitting of the light. The process returns to block 704 to send signals to the group of active markers again and check if more adjustments are needed.

If the calibration for the particular group of active markers is confirmed, in block 714, the system determines whether there are additional active marker groups that have not yet been checked for calibration. If there are additional groups to check, the process returns to block 704 to send calibration signals to the next group. Otherwise, in block 716 if there are not additional groups, the system may proceed with data capture, for example as shown in the flowchart in FIG. 7b.

Figure 7A:
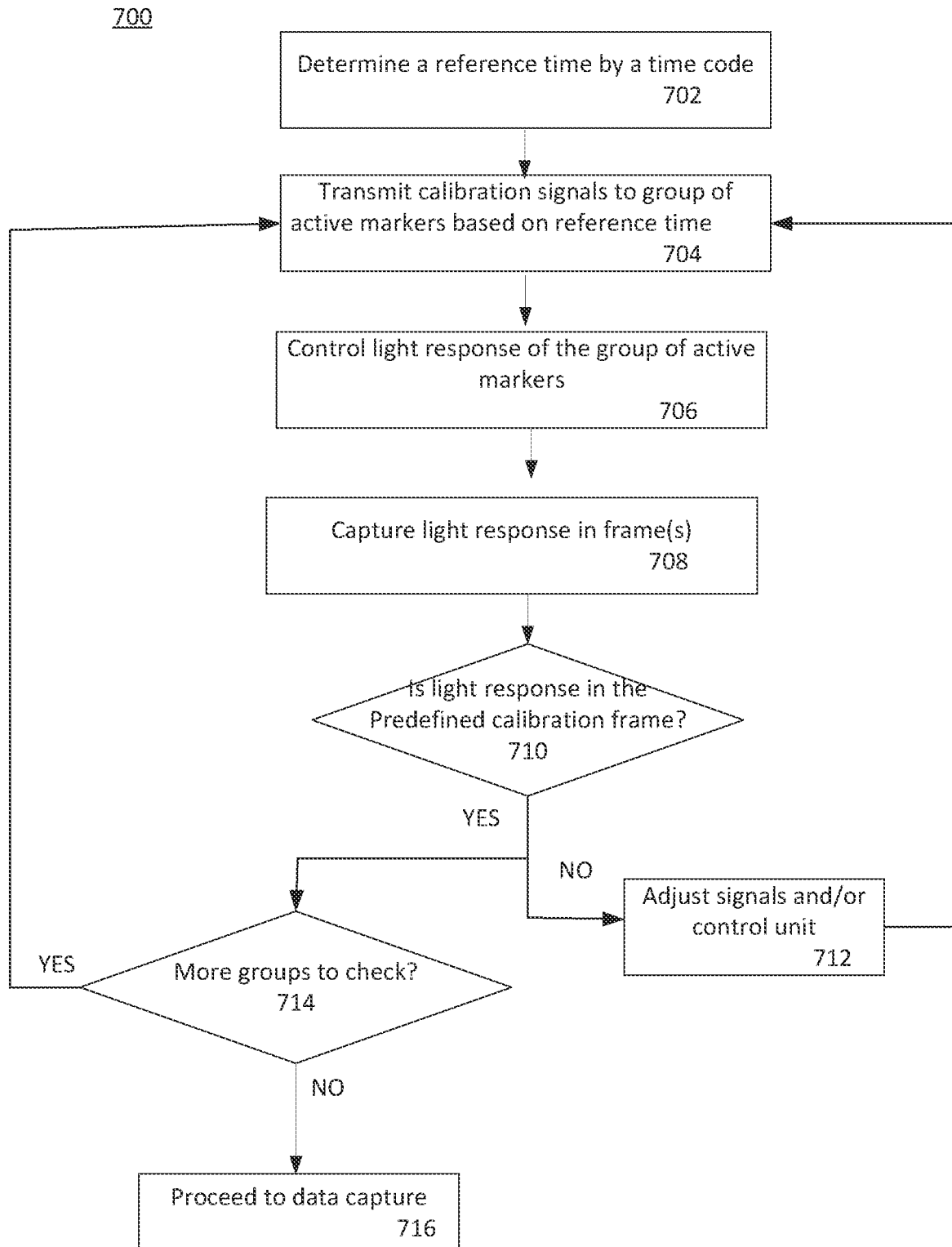
Figure 7B:
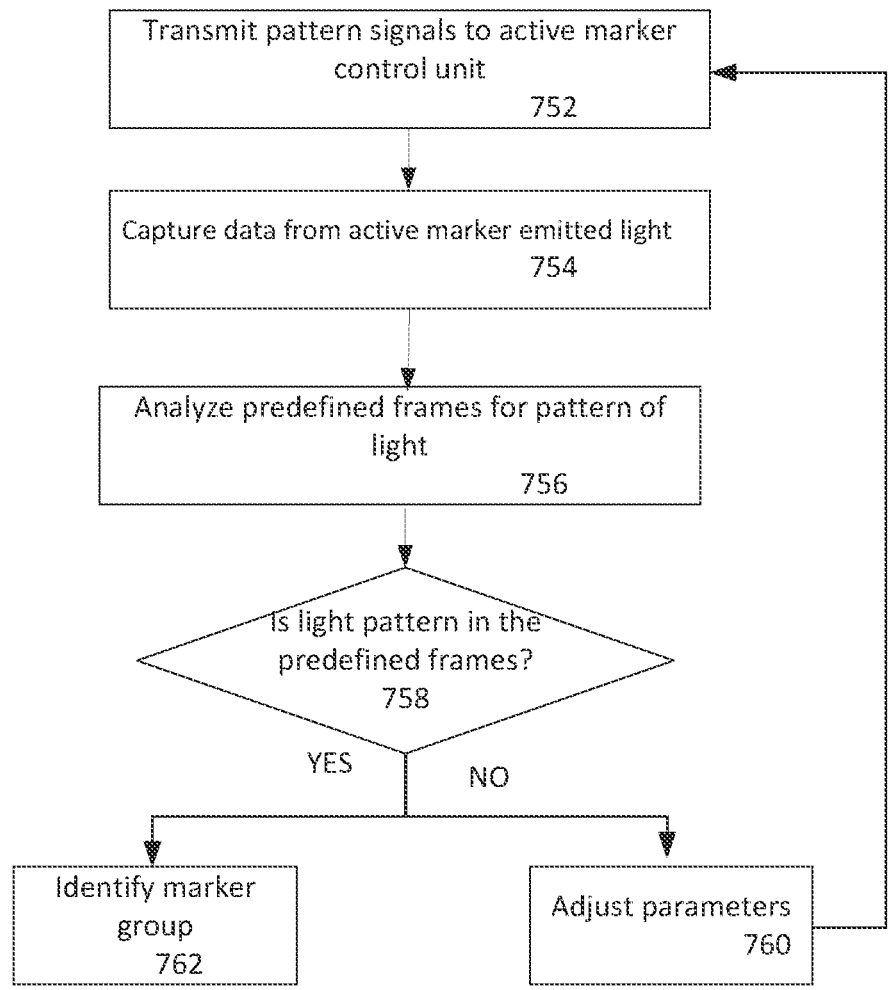

Once the devices are synchronized, the capture phase 750, as shown in the flowchart in FIG. 7b is employed to recognize light from active markers in performance capture. During the capture phase, a feedback loop may be used to check for drift of the light by the active markers. The feedback loop may consist of data capture system checking for an expected pattern of light within predefined frames. Adjustments to the control unit and/or signal controller may be made for any detected offsets.

Various groups of active markers can be made to emit light according to individual group light patterns at certain times, such as all groups may fire at the same time, groups may fire sequentially, assortments of groups may collectively fire together, e.g. all groups on a particular object or all groups in a sector of the live action scene, etc.

For example, each strand of active markers on an object may be labeled as to the part of the object that the strand is attached, such as an arm, leg, head, back, front torso, and waist of an actor. In some implementations, eight strands are strung on an actor.

In block 752, the signal controller transmits pattern signals, e.g. in the form of radio frequency signals, to the active marker control unit. The control unit receives the signals and modulates power to the active marker(s) according to the pattern. Light is emitted from the active markers and in block 754, the fluctuating light is captured in the form of data in captured frames by the sensor device of the performance capture system.

In some implementations, one or more particular sensor devices of the performance capture system may be assigned to track the group of markers. In block 756, the predefined frames that are expected by the software to include the pattern of light of the assigned sensor devices are analyzed, such as by computing device 130 in FIG. 1 and software running on the computing device. The frames that depict the light pattern include a sequence of illuminated and blank frames.

In decision block 758, it is determined whether the data in the predefined frames are consistent with the light pattern. If the predefined frames do not include the signature pattern, the parameters of the signals and/or control unit may be adjusted and the process may return back to block 752 to transmit corrected signals. If the pattern is detected in the predefined frames, in block 760 the group of active markers are identified.

The identified group of active markers may be labeled and tracked as the visual production proceeds. In some implementations, the identified group of active markers may be used as a spatial reference to identify further active marker groups. A subsequent phase in the process may be post production in which the captured data is utilized to generate computer graphics corresponding to the data.

In some implementations, various groups of active markers may be controlled by the same or different control units and assigned to different patterns. The resulting light patterns may be used to differentiate and identify the various groups of markers. The computing device (130 in FIG. 1) may need to differentiate between groups of markers in various frames from numerous sensor devices. Some sensor devices may capture overlapping light from the same group or light patterns from different groups of active markers. For example, a visual production may include 48 sensor devices, all capturing different or overlapping light patterns, which all need to be sorted and identified. As shown by the flowchart in FIG. 8, a method 800 of distinguishing groups of active markers is described.

In block 802, the data capture system specifies a first light pattern for a first group of markers and a second light pattern for a second group of markers. The system may also define individual initial key sequences and/or terminal key sequences for the first group and for the second group. The pattern and sequence data for the various groups are provided to the sync controller, computing device and/or performance capture system. The control unit may also receive sequence and pattern data for active marker groups that are under its control.

In block 804, the signal controller transmits respective assigned initial key sequences followed by the assigned pattern signals, and the assigned terminal key sequence for particular first and second groups. The signals are detected by a receiver of the control unit for the group to which the sequence is assigned. Upon receiving the initial key sequence signals, the control unit is ready to receive the pattern signals and provide power to the group of active markers in timed pulses according to the pattern. For example the control unit may transfer electric power to the active marker through coupled wired strands. After receiving the pattern signals, the control unit receives the terminal key sequence to mark the end of the pattern signal. In this manner, the control unit is not confused by signals that are not intended to be pattern signals and stops interpreting received signals as the part of the pattern to govern light.

In block 806, the sensor device(s) of the performance capture system captures first data from light of the first group and second data from light of the second group. The data is captured in sequential illuminated and blank frames.

In block 808, the first data is compared with the first light pattern and the second data is compared with second light pattern, such as by the computing device or the performance capture system. For example, the first light pattern anticipates that particular predefined frames of the performance capture device are expected to have data that represents illumination of light from the first group of active markers and other predefined blank frames are expected to have data (or absence of data) that represents no light (or an absence of light) from the first group.

In decision block 810, it is determined whether the detected light pattern in the predefined frames within particular time slots for each group. If the predefined frames for the first and/or second pattern do not include the light or absence of light according to the pattern in block 812, the process may return to block 804 to retransmit signals. If the light pattern is successfully detected in the expected frames, in block 814 the associated group of active markers is identified. Such identification may include labeling the markers according to the object and/or object part to which the identified group is attached.

Figure 8:
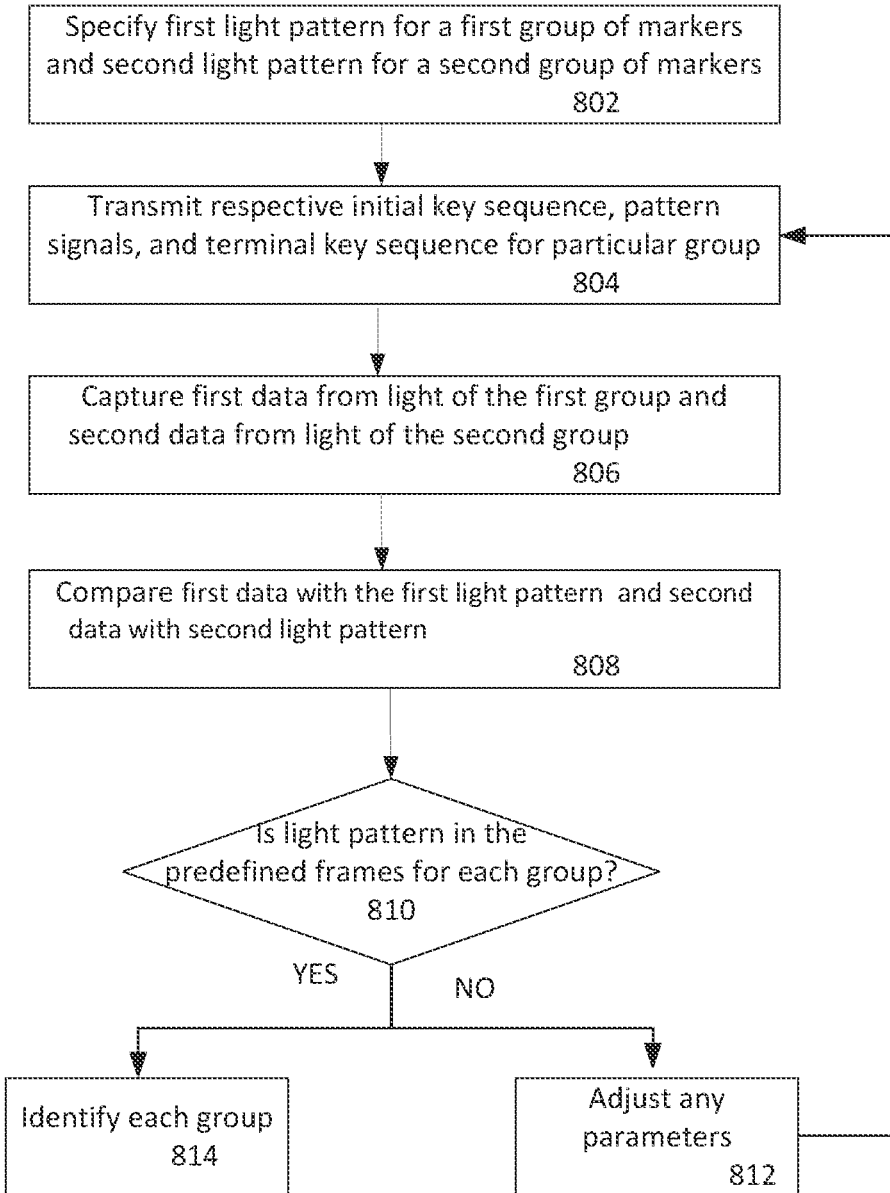
FIG. 8 is a flowchart of an example method to distinguish between groups of active markers in the data capture system, in accordance with some implementations.

Although the steps in FIGS. 7a, 7b, and 8 may be presented in a specific order, this order may be changed in different particular implementations. In some particular implementations, multiple steps shown as sequential in this specification can be performed at the same time.

Example Computer System

Figure 9:
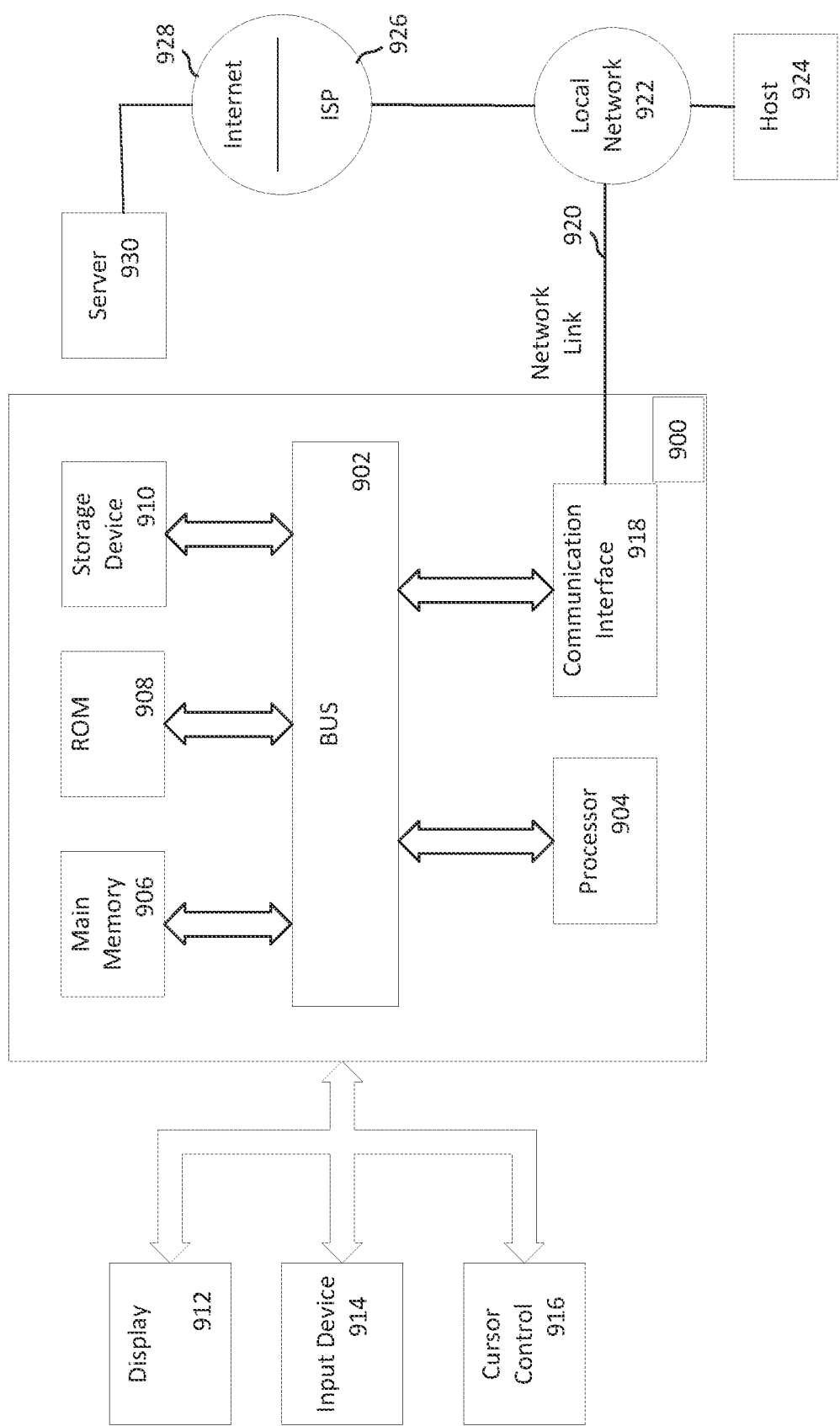
FIG. 9 is a block diagram illustrating an example computer system upon which computer systems of the systems illustrated in FIGS. 1 and 5 may be implemented, in accordance with some implementations.

As shown in FIG. 9, a computer system 900 may be employed upon which the performance capture system (such as 120 in FIG. 1) and/or the CG rendering system (such as 126 in FIG. 1) may be implemented. The computer system 900 includes a bus 902 or other communication mechanism for communicating information, and a processor 904 coupled with the bus 902 for processing information. The processor 904 may be, for example, a general purpose microprocessor.

The computer system 900 also includes a main memory 906, such as a random access memory (RAM) or other dynamic storage device, coupled to the bus 902 for storing information and instructions to be executed by the processor 904. The main memory 906 may also be used for storing temporary variables or other intermediate information during execution of instructions to be executed by the processor 904. Such instructions, when stored in non-transitory storage media accessible to the processor 904, render the computer system 900 into a special-purpose machine that is customized to perform the operations specified in the instructions.

The computer system 900 further includes a read only memory (ROM) 908 or other static storage device coupled to the bus 902 for storing static information and instructions for the processor 904. A storage device 910, such as a magnetic disk or optical disk, is provided and coupled to the bus 002 for storing information and instructions.

The computer system 900 may be coupled via the bus 902 to a display 912, such as a computer monitor, for displaying information to a computer user. An input device 914, including alphanumeric and other keys, is coupled to the bus 902 for communicating information and command selections to the processor 904. Another type of user input device is a cursor control 916, such as a mouse, a trackball, or cursor direction keys for communicating direction information and command selections to the processor 904 and for controlling cursor movement on the display 912. This input device typically has two degrees of freedom in two axes, a first axis (e.g., x) and a second axis (e.g., y), that allows the device to specify positions in a plane.

The computer system 900 may implement the techniques described herein using customized hard-wired logic, one or more ASICs or FPGAs, firmware and/or program logic which in combination with the computer system causes or programs the computer system 900 to be a special-purpose machine. According to one embodiment, the techniques herein are performed by the computer system 900 in response to the processor 904 executing one or more sequences of one or more instructions contained in the main memory 906. Such instructions may be read into the main memory 906 from another storage medium, such as the storage device 910. Execution of the sequences of instructions contained in the main memory 906 causes the processor 904 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may include non-volatile media and/or volatile media. Non-volatile media includes, for example, optical or magnetic disks, such as the storage device 910. Volatile media includes dynamic memory, such as the main memory 906. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire, and fiber optics, including the wires that include the bus 902. Transmission media can also take the form of acoustic or light waves, such as those generated during radio-wave and infrared data communications.

Various forms of media may be involved in carrying one or more sequences of one or more instructions to the processor 904 for execution. For example, the instructions may initially be carried on a magnetic disk or solid state drive of a remote computer. The remote computer can load the instructions into its dynamic memory and send the instructions over a network connection. A modem or network interface local to the computer system 900 can receive the data. The bus 902 carries the data to the main memory 906, from which the processor 904 retrieves and executes the instructions. The instructions received by the main memory 906 may optionally be stored on the storage device 910 either before or after execution by the processor 904.

The computer system 900 also includes a communication interface 918 coupled to the bus 902. The communication interface 918 provides a two-way data communication coupling to a network link 920 that is connected to a local network 922. For example, the communication interface 918 may be an integrated services digital network (ISDN) card, cable modem, satellite modem, or a modem to provide a data communication connection to a corresponding type of telephone line. Wireless links may also be implemented. In any such implementation, the communication interface 918 sends and receives electrical, electromagnetic, or optical signals that carry digital data streams representing various types of information.

The network link 920 typically provides data communication through one or more networks to other data devices. For example, the network link 920 may provide a connection through the local network 922 to a host computer 924 or to data equipment operated by an Internet Service Provider (ISP) 926. The ISP 926 in turn provides data communication services through the world wide packet data communication network now commonly referred to as the "Internet" 928. The local network 922 and Internet 928 both use electrical, electromagnetic, or optical signals that carry digital data streams. The signals through the various networks and the signals on the network link 920 and through the communication interface 918, which carry the digital data to and from the computer system 900, are example forms of transmission media.

The computer system 900 can send messages and receive data, including program code, through the network(s), the network link 920, and communication interface 918. In the Internet example, a server 930 might transmit a requested code for an application program through the Internet 928, ISP 926, local network 922, and communication interface 918. The received code may be executed by the processor 904 as it is received, and/or stored in the storage device 910, or other non-volatile storage for later execution.

For example, FIG. 9 illustrates the example visual content generation system 900 as might be used to generate imagery in the form of still images and/or video sequences of images. The visual content generation system 900 might generate imagery of live action scenes, computer generated scenes, or a combination thereof. In a practical system, users are provided with tools that allow them to specify, at high levels and low levels where necessary, what is to go into that imagery. and might use the visual content generation system 900 to capture interaction between two human actors performing live on a sound stage and replace one of the human actors with a computer-generated anthropomorphic non-human being that behaves in ways that mimic the replaced human actor's movements and mannerisms, and then add in a third computer-generated character and background scene elements that are computer-generated, all in order to tell a desired story or generate desired imagery.

Still images that are output by the visual content generation system 900 might be represented in computer memory as pixel arrays, such as a two-dimensional array of pixel color values, each associated with a pixel having a position in a two-dimensional image array. Pixel color values might be represented by three or more (or fewer) color values per pixel, such as a red value, a green value, and a blue value (e.g., in RGB format). Dimension of such a two-dimensional array of pixel color values might correspond to a preferred and/or standard display scheme, such as 1920 pixel columns by 1280 pixel rows. Images might or might not be stored in a compressed format, but either way, a desired image may be represented as a two-dimensional array of pixel color values. In another variation, images are represented by a pair of stereo images for three-dimensional presentations and in other variations, some or all of an image output might represent three-dimensional imagery instead of just two-dimensional views.

A stored video sequence might include a plurality of images such as the still images described above, but where each image of the plurality of images has a place in a timing sequence and the stored video sequence is arranged so that when each image is displayed in order, at a time indicated by the timing sequence, the display presents what appears to be moving and/or changing imagery. In one representation, each image of the plurality of images is a video frame having a specified frame number that corresponds to an amount of time that would elapse from when a video sequence begins playing until that specified frame is displayed. A frame rate might be used to describe how many frames of the stored video sequence are displayed per unit time. Example video sequences might include 24 frames per second (24 FPS), 50 FPS, 140 FPS, or other frame rates. In some embodiments, frames are interlaced or otherwise presented for display, but for the purpose of clarity of description, in some examples, it is assumed that a video frame has one specified display time and it should be understood that other variations are possible.

One method of creating a video sequence is to simply use a video camera to record a live action scene, i.e., events that physically occur and can be recorded by a video camera. The events being recorded can be events to be interpreted as viewed (such as seeing two human actors talk to each other)

and/or can include events to be interpreted differently due to clever camera operations (such as moving actors about a stage to make one appear larger than the other despite the actors actually being of similar build, or using miniature objects with other miniature objects so as to be interpreted as a scene containing life-sized objects).

Creating video sequences for story-telling or other purposes often calls for scenes that cannot be created with live actors, such as a talking tree, an anthropomorphic object, space battles, and the like. Such video sequences might be generated computationally rather than capturing light from live scenes. In some instances, an entirety of a video sequence might be generated computationally, as in the case of a computer-animated feature film. In some video sequences, it is desirable to have some computer-generated imagery and some live action, perhaps with some careful merging of the two.

While computer-generated imagery might be creatable by manually specifying each color value for each pixel in each frame, this is likely too tedious to be practical. As a result, a creator uses various tools to specify the imagery at a higher level. As an example, an artist might specify the positions in a scene space, such as a three-dimensional coordinate system, of objects and/or lighting, as well as a camera viewpoint, and a camera view plane. Taking all of that as inputs, a rendering engine may compute each of the pixel values in each of the frames. In another example, an artist specifies position and movement of an articulated object having some specified texture rather than specifying the color of each pixel representing that articulated object in each frame.

In a specific example, a rendering engine performs ray tracing wherein a pixel color value is determined by computing which objects lie along a ray traced in the scene space from the camera viewpoint through a point or portion of the camera view plane that corresponds to that pixel. For example, a camera view plane might be represented as a rectangle having a position in the scene space that is divided into a grid corresponding to the pixels of the ultimate image to be generated, and if a ray defined by the camera viewpoint in the scene space and a given pixel in that grid first intersects a solid, opaque, blue object, that given pixel is assigned the color blue. Of course, for modern computer-generated imagery, determining pixel colors—and thereby generating imagery—can be more complicated, as there are lighting issues, reflections, interpolations, and other considerations.

Example Live Action Capture System

Figure 10:
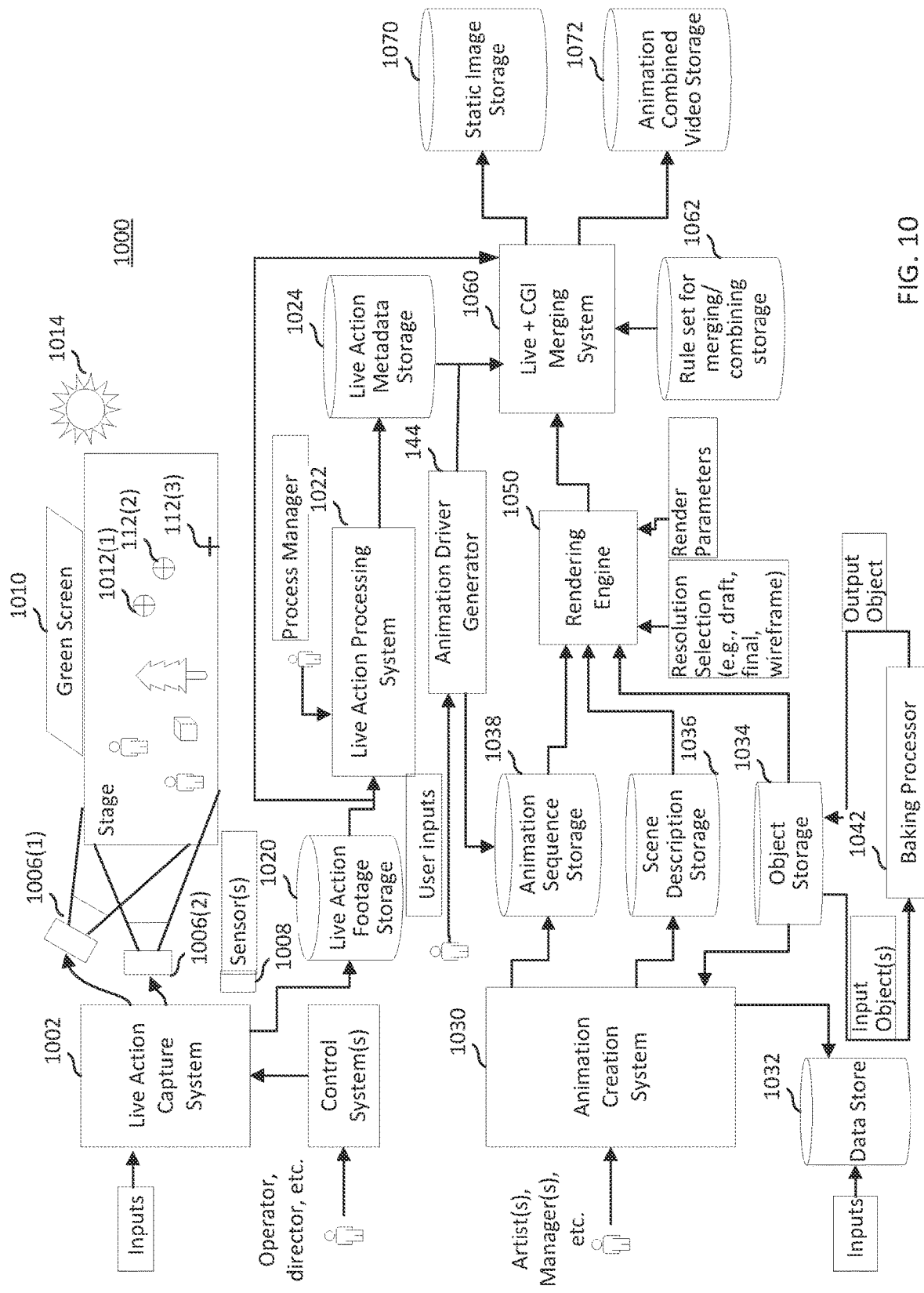
FIG. 10 illustrates an example visual content generation system as might be used to generate imagery in the form of still images and/or video sequences of images, in accordance with some implementations.

As illustrated in FIG. 10, a live action capture system 1002 captures a live scene that plays out on a stage 1004. The live action capture system 1002 is described herein in greater detail, but might include computer processing capabilities, image processing capabilities, one or more processors, program code storage for storing program instructions executable by the one or more processors, as well as user input devices and user output devices, not all of which are shown.

In a specific live action capture system, cameras 1006(1) and 1006(2) capture the scene, while in some systems, there might be other sensor(s) 1008 that capture information from the live scene (e.g., infrared cameras, infrared sensors, motion capture ("mo-cap") detectors, etc.). On the stage 1004, there might be human actors, animal actors, inanimate objects, background objects, and possibly an object such as a green screen 1010 that is designed to be captured in a live scene recording in such a way that it is easily overlaid with computer-generated imagery. The stage 1004 might also contain objects that serve as fiducials, such as fiducials 1012(1)-(3), that might be used post-capture to determine where an object was during capture. A live action scene might be illuminated by one or more lights, such as an overhead light 1014.

During or following the capture of a live action scene, the live action capture system 1002 might output live action footage to a live action footage storage 1020. A live action processing system 1022 might process live action footage to generate data about that live action footage and store that data into a live action metadata storage 1024. The live action processing system 1022 might include computer processing capabilities, image processing capabilities, one or more processors, program code storage for storing program instructions executable by the one or more processors, as well as user input devices and user output devices, not all of which are shown. The live action processing system 1022 might process live action footage to determine boundaries of objects in a frame or multiple frames, determine locations of objects in a live action scene, where a camera was relative to some action, distances between moving objects and fiducials, etc. Where elements are sensed or detected, the metadata might include location, color, and intensity of the overhead light 1014, as that might be useful in post-processing to match computer-generated lighting on objects that are computer-generated and overlaid on the live action footage. The live action processing system 1022 might operate autonomously, perhaps based on predetermined program instructions, to generate and output the live action metadata upon receiving and inputting the live action footage. The live action footage can be camera-captured data as well as data from other sensors.

An animation creation system 1030 is another part of the visual content generation system 1000. The animation creation system 1030 might include computer processing capabilities, image processing capabilities, one or more processors, program code storage for storing program instructions executable by the one or more processors, as well as user input devices and user output devices, not all of which are shown. The animation creation system 1030 might be used by animation artists, managers, and others to specify details, perhaps programmatically and/or interactively, of imagery to be generated. From user input and data from a database or other data source, indicated as a data store 1032, the animation creation system 1030 might generate and output data representing objects (e.g., a horse, a human, a ball, a teapot, a cloud, a light source, a texture, etc.) to an object storage 1034, generate and output data representing a scene into a scene description storage 1036, and/or generate and output data representing animation sequences to an animation sequence storage 1038.

Scene data might indicate locations of objects and other visual elements, values of their parameters, lighting, camera location, camera view plane, and other details that a rendering engine 1050 might use to render CGI imagery. For example, scene data might include the locations of several articulated characters, background objects, lighting, etc. specified in a two-dimensional space, three-dimensional space, or other dimensional space (such as a 2.5-dimensional space, three-quarter dimensions, pseudo-3D spaces, etc.) along with locations of a camera viewpoint and view place from which to render imagery. For example, scene data might indicate that there is to be a red, fuzzy, talking dog in the right half of a video and a stationary tree in the left half of the video, all illuminated by a bright point light source that is above and behind the camera viewpoint. In some cases, the camera viewpoint is not explicit, but can be determined from a viewing frustum. In the case of imagery that is to be rendered to a rectangular view, the frustum would be a truncated pyramid. Other shapes for a rendered view are possible and the camera view plane could be different for different shapes.

The animation creation system 1030 might be interactive, allowing a user to read in animation sequences, scene descriptions, object details, etc. and edit those, possibly returning them to storage to update or replace existing data. As an example, an operator might read in objects from object storage into a baking processor that would transform those objects into simpler forms and return those to the object storage 1034 as new or different objects. For example, an operator might read in an object that has dozens of specified parameters (movable joints, color options, textures, etc.), select some values for those parameters and then save a baked object that is a simplified object with now fixed values for those parameters.

Rather than have to specify each detail of a scene, data from the data store 1032 might be used to drive object presentation. For example, if an artist is creating an animation of a spaceship passing over the surface of the Earth, instead of manually drawing or specifying a coastline, the artist might specify that the animation creation system 1030 is to read data from the data store 1032 in a file containing coordinates of Earth coastlines and generate background elements of a scene using that coastline data.

Animation sequence data might be in the form of time series of data for control points of an object that has attributes that are controllable. For example, an object might be a humanoid character with limbs and joints that are movable in manners similar to typical human movements. An artist can specify an animation sequence at a high level, such as "the left hand moves from location (X1, Y1, Z1) to (X2, Y2, Z2) over time T1 to T2", at a lower level (e.g., "move the elbow joint 2.5 degrees per frame") or even at a very high level (e.g., "character A should move, consistent with the laws of physics that are given for this scene, from point P1 to point P2 along a specified path").

Animation sequences in an animated scene might be specified by what happens in a live action scene. An animation driver generator 1044 might read in live action metadata, such as data representing movements and positions of body parts of a live actor during a live action scene, and generate corresponding animation parameters to be stored in the animation sequence storage 1038 for use in animating a CGI object. This can be useful where a live action scene of a human actor is captured while wearing mo-cap fiducials (e.g., high-contrast markers outside actor clothing, high-visibility paint on actor skin, face, etc.) and the movement of those fiducials is determined by the live action processing system 1022. The animation driver generator 1044 might convert that movement data into specifications of how joints of an articulated CGI character are to move over time.

A rendering engine 1050 can read in animation sequences, scene descriptions, and object details, as well as rendering engine control inputs, such as a resolution selection and a set of rendering parameters. Resolution selection might be useful for an operator to control a trade-off between speed of rendering and clarity of detail, as speed might be more important than clarity for a movie maker to test a particular interaction or direction, while clarity might be more important that speed for a movie maker to generate data that will be used for final prints of feature films to be distributed. The rendering engine 1050 might include computer processing capabilities, image processing capabilities, one or more processors, program code storage for storing program instructions executable by the one or more processors, as well as user input devices and user output devices, not all of which are shown.

The visual content generation system 1000 can also include a merging system 1060 that merges live footage with animated content. The live footage might be obtained and input by reading from the live action footage storage 1020 to obtain live action footage, by reading from the live action metadata storage 1024 to obtain details such as presumed segmentation in captured images segmenting objects in a live action scene from their background (perhaps aided by the fact that the green screen 1010 was part of the live action scene), and by obtaining CGI imagery from the rendering engine 1050.

A merging system 1060 might also read data from a rulesets for merging/combining storage 1062. A very simple example of a rule in a ruleset might be "obtain a full image including a two-dimensional pixel array from live footage, obtain a full image including a two-dimensional pixel array from the rendering engine 1050, and output an image where each pixel is a corresponding pixel from the rendering engine 1050 when the corresponding pixel in the live footage is a specific color of green, otherwise output a pixel value from the corresponding pixel in the live footage."

The merging system 1060 might include computer processing capabilities, image processing capabilities, one or more processors, program code storage for storing program instructions executable by the one or more processors, as well as user input devices and user output devices, not all of which are shown. The merging system 1060 might operate autonomously, following programming instructions, or might have a user interface or programmatic interface over which an operator can control a merging process. In some embodiments, an operator can specify parameter values to use in a merging process and/or might specify specific tweaks to be made to an output of the merging system 1060, such as modifying boundaries of segmented objects, inserting blurs to smooth out imperfections, or adding other effects. Based on its inputs, the merging system 1060 can output an image to be stored in a static image storage 1070 and/or a sequence of images in the form of video to be stored in an animated/combined video storage 1072.

Thus, as described, the visual content generation system 1000 can be used to generate video that combines live action with computer-generated animation using various components and tools, some of which are described in more detail herein. While the visual content generation system 1000 might be useful for such combinations, with suitable settings, it can be used for outputting entirely live action footage or entirely CGI sequences. The code may also be provided and/or carried by a transitory computer readable medium, e.g., a transmission medium such as in the form of a signal transmitted over a network.

Example Graphical User Interface

Figure 11:
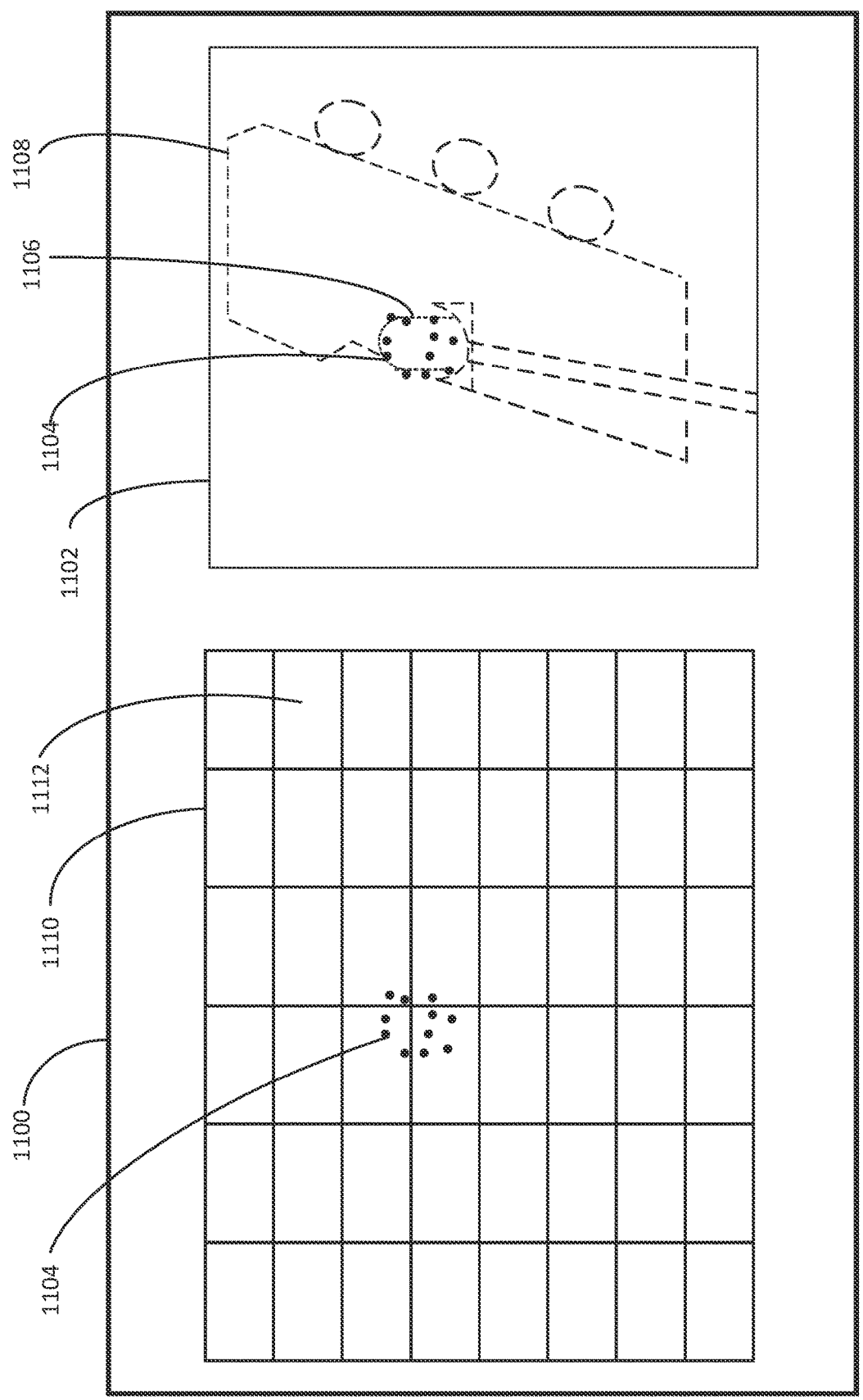
FIG. 11 is an illustration of an exemplary graphical user interface showing images from performance capture sensor devices, in accordance with some implementations.

In some implementations, as shown in FIG. 11, a graphical user interface (GUI) 1100 may be employed to display captured data of light emitted from active markers in a live action scene. The GUI may include an image 1102 which depicts the light data 1104 of light emitted from markers attached to an actor 1106 the scene. For example, the image may be a composite of data collected by multiple sensor devices of a performance capture system. The image may also be merged with images from one or more picture cameras recording the scene to depict the light data 1104 with context image data of objects, such as the actor 1106 riding in a tank 1108.

The GUI may also depict a grid 1110 having cells 1112 for each sensor device of the performance capture system. In the example in FIG. 11, forty-eight sensor devices capture marker data from the scene with four cells from four sensor devices capturing the light data 1104 of light from active markers attached actor 1106.

CONCLUSION

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

Although the description has been described with respect to particular embodiments thereof, these particular embodiments are merely illustrative, and not restrictive. For example, in some implementations, a plurality of picture cameras may be used to capture images from various angles of the same live action scene or to capture different portions of the live action scene and the images may be stitched together or particular images selected for the output image. In various implementations, additional equipment, techniques and technologies may be employed to accommodate requirements of a particular visual production and live action scene, such as underwater scenes.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nano-engineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above. A computer readable medium can comprise any medium for carrying instructions for execution by a computer, and includes a tangible computer readable storage medium and a transmission medium, such as a signal transmitted over a network such as a computer network, an optical signal, an acoustic signal, or an electromagnetic signal.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A method for recognizing light from a group of active markers in performance capture associated with a visual production, the method comprising:
   synchronizing a signal controller with a frame rate of one or more sensor devices of a performance capture system, by:
      determining a reference time according to a time code that corresponds with a reference frame of the one or more sensor devices;
      sending calibration signals from the signal controller to the group of active markers to emit calibration light based on the reference time; and
      determining whether the calibration light is received in one or more expected frames;
   transmitting pattern signals by the signal controller, to instruct the group of active markers to emit light of at least one wavelength range according to a pattern, in which a presence of the light coincides with one or more predefined illuminated frames and an absence of the light coincides with one or more predefined blank frames of the performance capture system;
   generating, by one or more sensor devices, data associated with light captured in one or more illuminated frames and absence of light in one or more blank frames; and
   identifying the group of active markers, by one or more processors determining that the data associated with the one or more predefined illuminated frames and the one or more predefined blank frames correspond with the pattern.

2. The method of claim 1, wherein the synchronizing further includes a phase locked loop of the calibration signals of the signal controller and the frame rate of the one or more sensor devices.

3. The method of claim 1, wherein based on the synchronizing, the method further comprising, determining an out of sync sensor device of the one or more sensor devices, and adjusting the out of sync sensor device by one or more of realigning the out of sync sensor device, or reducing reprojection error to achieve predicted data collection.

4. The method of claim 1, further comprising,
   determining that the calibration light is out of sync with the reference time; and
   changing the calibration signals to adjust the emitting of the calibration light.

5. The method of claim 1, wherein determining the data corresponds to the pattern includes predicting, for respective frames, that the light is to be present or absent based on the pattern, and confirming that the light is present or absent in the respective frames.

6. The method of claim 1, further comprising,
   synchronizing the frame rate of the one or more sensor devices with a shutter action of a picture camera, wherein the frame rate of the one or more sensor devices is faster than the shutter action of the picture camera, such that the pattern is detectable within a single cycle of the picture camera.

7. The method of claim 1, further comprising:
   determining a position of a first active marker of the group of active markers; and
   identifying respective positions of other active markers of the group of active markers based on the determined position of the first active marker.

8. The method of claim 1, wherein the group of active markers are configured to emit multiple wavelengths of the light.

9. The method of claim 1, wherein the pattern includes on and off intervals of light of uniform lengths.

10. A data capture system to recognize light from a group of active markers for performance capture associated with a visual production, the system comprising:
    a signal controller to transmit signals for the group of active markers to emit light of at least one wavelength range in a pattern including a presence of light that coincides with one or more illuminated predefined frames and an absence of the light that coincides with one or more predefined blank frames of a performance capture system, the signal controller being synchronized with a frame rate of the performance capture system;
    the group of active markers to emit pulses of the light;
    at least one sensor device of the performance capture system to generate data representing captured presence of the light and absence of the light from the group of active markers in respective one or more illuminated frames and one or more blank frames; and
    a computing device to identify the group of active markers based on a comparison of the data with the pattern.

11. The system of claim 10, wherein the signal controller and the performance capture system are synchronized by determining a reference time according to a time code that corresponds with a reference frame of the at least one sensor device and the group of active markers is instructed by calibration signals of the signal controller to emit light based on the reference time.

12. The system of claim 10, further comprising a picture camera device having a shutter action that is synchronized with the frame rate of the at least one sensor device, wherein the frame rate of the at least one sensor device is faster than the shutter action of the picture camera device, such that the pattern is detectable within a single frame of the picture camera device.

13. The system of claim 10, further comprising a control unit in electrical communication with the group of active markers, to receive the signals and control the group of active markers to emit light according to the pattern.

14. The system of claim 13, further comprising a wired strand coupled to the control unit and each active marker of the group of active markers.

15. A non-transitory computer-readable storage medium carrying program instructions thereon to recognize light from a group of active markers in performance capture associated with a visual production, the instructions when executed by one or more processors cause the one or more processors to perform operations comprising:
- synchronizing with a time code of a signal controller and a performance capture system;
- determining a pattern for the group of active markers to emit light of at least one wavelength range, in which presence of the light coincides with one or more predefined illuminated frames and absence of the light coincides with one or more predefined blank frames of the performance capture system;
- transmitting the pattern to the signal controller to instruct the group of active markers to emit the light according to the pattern;
- receiving data associated with captured light from the performance capture system, the data representing the captured light in one or more illuminated frames and the absence of the light in one or more blank frames; and
- identifying the group of active markers based on determining that the data correspond with the pattern in the one or more predefined illuminated frames and the one or more predefined blank frames.

16. The computer-readable storage medium of claim 15, wherein the operations further comprise:
- determining a reference time according to the time code and transmitting the reference time to the signal controller and performance capture system to synchronize the light with the reference time.

17. The computer-readable storage medium of claim 15, wherein the operations further comprise:
- prior to identifying the group of active markers, determining that one or more other predefined illuminated frames and one or more other predefined blank frames lack the pattern; and
- instructing the signal controller to adjust synchronization with the performance capture system.

18. The computer-readable storage medium of claim 15, wherein the operations further comprise:
- associating labels with the identified group of active markers by at least one of an object and part of the object to which the group of active markers is attached.

19. The computer-readable storage medium of claim 18, wherein the operations further comprise:
- transmitting the data and labels to a computer graphics rendering system to be mapped to a virtual model.

20. The computer-readable storage medium of claim 15, wherein the operations further comprise:
- receiving status information from a control unit of the group of active markers; and
- providing a notification of the status information.

* * * * *